United States Patent
Hodes et al.

(10) Patent No.: US 11,497,699 B2
(45) Date of Patent: Nov. 15, 2022

(54) OXIDATIVE DYE IN RED SHADES WITH IMPROVED FASTNESS AND IMPROVED HOMOGENEITY

(71) Applicant: Henkel AG & Co. KGaA, Duesseldorf (DE)

(72) Inventors: Jing Hodes, Hagen (DE); Sandra Hilbig, Bochum (DE); Daniela Kessler-Becker, Leverkusen (DE); Melanie Moch, Dormagen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/414,294

(22) PCT Filed: Nov. 12, 2019

(86) PCT No.: PCT/EP2019/080970
§ 371 (c)(1),
(2) Date: Jun. 15, 2021

(87) PCT Pub. No.: WO2020/126225
PCT Pub. Date: Jun. 25, 2020

(65) Prior Publication Data
US 2022/0016008 A1    Jan. 20, 2022

(30) Foreign Application Priority Data
Dec. 17, 2018 (DE) .................. 10 2018 221 959.1

(51) Int. Cl.
| A61Q 5/10 | (2006.01) |
| A61K 8/49 | (2006.01) |
| A61K 8/22 | (2006.01) |
| A61K 8/365 | (2006.01) |

(52) U.S. Cl.
CPC .............. *A61K 8/494* (2013.01); *A61K 8/22* (2013.01); *A61K 8/365* (2013.01); *A61Q 5/10* (2013.01); *A61K 2800/88* (2013.01)

(58) Field of Classification Search
CPC .. A61Q 5/10; A61Q 5/065; A61K 2800/4324; A61K 8/22; A61K 8/365; A61K 2800/87
USPC ........................................................ 8/405
See application file for complete search history.

(56) References Cited

U.S. PATENT DOCUMENTS

| 8,444,709 B2* | 5/2013 | Lim | A61K 8/494 8/408 |
| 8,444,710 B2* | 5/2013 | Lim | A61K 8/494 8/408 |
| 8,444,713 B2* | 5/2013 | Lim | A61Q 5/10 8/408 |
| 8,444,714 B2* | 5/2013 | Lim | A61K 8/4946 8/408 |
| 8,460,397 B2* | 6/2013 | Lim | A61Q 5/10 8/408 |
| 8,784,505 B2* | 7/2014 | Geibel | A61K 8/494 8/405 |
| 2004/0170670 A1* | 9/2004 | Smith | A61K 8/87 424/443 |

FOREIGN PATENT DOCUMENTS

| DE | 102006017901 | 10/2007 |
| EP | 1321131 A1 | 6/2003 |
| EP | 1875892 A2 | 1/2008 |
| EP | 2471504 A1 | 7/2012 |
| JP | 2004210700 A | 7/2004 |
| WO | 2003015734 A1 | 2/2003 |
| WO | 2006106366 A1 | 10/2006 |
| WO | 2016177344 A1 | 11/2016 |

OTHER PUBLICATIONS

EPO, International Search Report issued in International Application No. PCT/EP2019/080970, dated Jan. 30, 2021.
Mintel GNPD: "Hair Colourant_Sanotint", Hair Products, Jun. 2008.
Mintel GNPD: "Multi-Tones Colour Kit", Hair Products, Mar. 2007.
Mintel GNPD: "Colour Permanent Conditioning Hair Colour", Hair Products, Sep. 2004.
Mintel GNPD: "MatriCur", Dr Suwelack & Health Care, Vitamins & Dietary Supplements, Jul. 2000.

* cited by examiner

*Primary Examiner* — Eisa B Elhilo
(74) *Attorney, Agent, or Firm* — Lorenz & Kopf, LLP

(57) ABSTRACT

The subject of the present application is an agent for the oxidative dyeing of keratinous fibers, in particular human hair, which contains in a cosmetic carrier (A) at least one oxidation dye precursor with 4,5-diaminopyrazole as the basic structural element according to the structural formula (I) and furthermore (B) glucoheptonic acid and/or at least one of its physiologically tolerated salts and/or lactones. The composition as contemplated herein further comprises (C) at least one oxidizing agent other than atmospheric oxygen.

20 Claims, No Drawings

OXIDATIVE DYE IN RED SHADES WITH IMPROVED FASTNESS AND IMPROVED HOMOGENEITY

CROSS-REFERENCE TO RELATED APPLICATION

This application is a U.S. National-Stage entry under 35 U.S.C. § 371 based on International Application No. PCT/EP2019/080970, filed Nov. 12, 2019, which was published under PCT Article 21(2) and which claims priority to German Application No. 10 2018 221 959.1, filed Dec. 17, 2018, which are all hereby incorporated in their entirety by reference.

TECHNICAL FIELD

The subject of the present application is an agent for the oxidative dyeing of keratinous fibers, in particular human hair, which contains in a cosmetic carrier (A) at least one oxidation dye precursor with 4,5-diaminopyrazole as the basic structural element according to the structural formula (I) and furthermore (B) glucoheptonic acid and/or at least one of its physiologically tolerated salts and/or lactones. The composition as contemplated herein further comprises (C) at least one oxidizing agent other than atmospheric oxygen.

BACKGROUND

A second object of the present disclosure is a multi-component packaging unit (kit-of-parts) comprising at least two separately assembled components, wherein the first component (K1) contains the previously described ingredients (A) and (B) and the second component (K2) contains the previously described ingredient (C).

A third object of the present disclosure is a multi-component packaging unit (kit-of-parts) comprising at least two separately assembled components, wherein the first component (K1) contains the previously described ingredient (A) and optionally the previously described ingredient (C) and the second component (K2) contains the previously described ingredient (B).

A fourth object of the present disclosure is a multi-component packaging unit (kit-of-parts) comprising at least three separately assembled components, wherein the first component (K1) contains the previously described ingredient (A), the second component (K2) contains the previously described ingredient (B), and the third component (K3) contains the previously described ingredient (C).

A further object of the present disclosure is a process for oxidative hair coloring, in which an agent for the oxidative coloring of keratinous fibers, in particular human hair, is applied to the fibers, in particular human hair, which agent contains in a cosmetic carrier (A) at least one oxidation dye precursor with 4,5-diaminopyrazole as the basic structural element according to the structural formula (I), furthermore (B) glucoheptonic acid and/or at least one of its physiologically tolerated salts and/or lactones and furthermore (C) at least one oxidizing agent which is different from atmospheric oxygen, the colorant being rinsed out with water after a contact time of about 1 to about 60 minutes and the hair optionally being treated with further cleansing and care products and then dried.

Changing the color of keratin fibers, especially hair, is an important area of modern cosmetics. As a result, the appearance of the hair can be adapted both to current fashion trends and to the individual wishes of the individual. The expert knows different possibilities for changing the hair color. The hair color can be changed temporarily by using direct dye. Here, already fully formed dyes from the dye diffuse into the hair fiber. The dyeing with direct dyes is associated with little damage to the hair, but a disadvantage is the short shelf life and the quick washability of the dyeings obtained with direct dyes.

If consumers desire a long-lasting color result or a shade lighter than their original hair color, oxidative color modifiers are commonly used. So-called oxidation dyes are used for permanent, intensive dyeings with appropriate fastness properties. Such colorants usually contain oxidation dye precursors, so-called developer components (oxidation bases) and coupler components, which form the actual dyes under the influence of oxidizing agents among themselves. Oxidation dyes are exemplified by long-lasting dyeing results.

Extensive prior art already exists on oxidative colorants. Many attempts have been made to optimize the color intensity and fastness properties of fashion shades.

However, despite the large number of optimization trials already carried out, there is still room for improvement about the fastness properties of the dyeing of oxidatively dyed keratin fibers—especially if they are to be dyed in a mode shade in the red range. In particular, the wash fastness of red shades based on 4,5-diaminopyrazoles as the developer component (oxidation base) cannot yet be classified as optimal.

BRIEF SUMMARY

Agents, kits-of-parts, and methods for the oxidative dyeing of keratinous fibers are provided. In an exemplary embodiment, an agent for the oxidative dying of keratinous fibers includes an oxidation dye precursor of structure (I) and/or one of its physiologically tolerable salts, where structure (I) is:

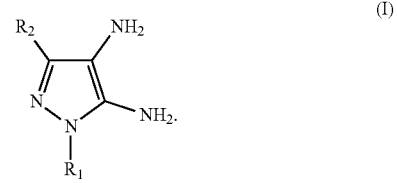

$R_1$ and $R_2$ are independently hydrogen or a linear or branched C1-C10 alkyl group which may be substituted with one to ten hydroxyl groups, and where $R_1$ and $R_2$ are not both hydrogen at the same time. The agent further includes glucoheptonic acid and/or at least one of its physiologically tolerated salts and/or lactones, and at least one oxidizing agent other than atmospheric oxygen.

A multicomponent kit-of-parts is provided in another embodiment. The kit-of-parts includes at least two separately prepared components (K1) and (K2), wherein the first component (K1) in a cosmetic carrier includes an oxidation dye precursor of the structure (I) and/or one of its physiologically tolerated salts, where structure (I) is:

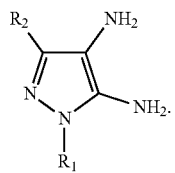

(I)

$R_1$ and $R_2$ are independently hydrogen or a linear or branched C1-C10 alkyl group which may be substituted with one to ten hydroxyl groups. $R_1$ and $R_2$ are not both hydrogen at the same time. The kit-of-parts further optionally includes an oxidizing agent selected from persalts, peroxodisulfate salts and/or peroxomonosulfate salts. The second component (K2) includes water, and the kit-of-parts also includes glucoheptonic acid and/or at least one of its physiologically tolerated salts and/or lactones.

A method of the oxidative dyeing of keratinous fibers is provided in yet another embodiment. The method includes applying an agent to the keratinous fibers, where the agent includes an oxidation dye precursor, glucoheptonic acid and/or at least one of its physiologically tolerated salts and/or lactones, and at least one oxidizing agent other than atmospheric oxygen. The agent is left on the fibers for from about 1 to about 60 minutes, and then rinsed from the fibers with water and/or a cleansing composition. An aftertreatment agent is optionally applied to the fibers, and optionally rinsed out of the fibers.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was to provide oxidative colorants for obtaining red shades based on 4,5-diaminopyrazoles as a developer component with improved fastness properties, with improved wash fastness.

The wash fastness of a color shade is understood as the color change of the hair strand dyed with this shade under the influence of several hair washes. This color change can be both a shift of the color towards another hue and the fading of the coloration. Both color changes are equally unwanted by the user. Shades with good wash fastness do not or hardly change in color even after repeated hair washes. The hair can be washed with the help of a shampoo, a conditioning shampoo, or a conditioner.

Another problem that must be overcome in the formulation of oxidative hair dyes concerns the homogeneity of the dyeing result on the hair. From the root to the tip of the hair, the hair fiber is damaged to varying degrees. Hair in the roots has just grown back and has not yet been exposed to any or only minor weather influences, chemical (dyeing, bleaching, perming, washing, swimming pool water) or physical (combing, blow-drying) influences. The area of the hair lengths is more damaged the further away it is from the hairline and therefore the older it is. The hair at the tips is the oldest part of the hair and therefore has the most damage.

In damaged hair, the cuticle, the hair's cuticle layer, is destroyed to a greater or lesser extent. This leads to a generally stronger color elevator on damaged hair. Therefore, if the roots and tips are colored with the same dye, there is always a risk of an uneven color result in more damaged hair.

For the purposes of the present application, the hair tips are considered part of the hair lengths. When talking about hair lengths, the hair ends are always included.

As contemplated herein, the hairline is understood to be the part of the hair located directly at the scalp (the first 0 to 5 cm of the hair).

Accordingly, the hair length area is understood to be the area of the hair fiber that is more than 5 cm from the scalp. As contemplated herein, the area of the hair ends is understood to be the last 3 cm of the hair fiber.

It was a further task of the present disclosure to provide the hairdresser or the home user with an oxidative hair coloring agent with which the most homogeneous, uniform coloring possible can be achieved along the hair fiber.

To improve the homogeneity of a dye or to reduce the selectivity of a dye or to improve the leveling capacity of a dye, the skilled person knows further methods. EP 2471504A1 deals with the task of providing oxidative hair dyes with a high leveling capacity, which achieve a uniform hair coloration both on the damaged parts of the hair fiber and on the undamaged or slightly damaged hairline. EP 2471504A1 solves this problem with an active ingredient combination of an amino acid surfactant, a cation surfactant, and an oil.

Keratinous fibers can be dyed in shades of red if, in the dyes (A), at least one oxidation dye precursor of structure (I) and/or one of its physiologically tolerated salts is

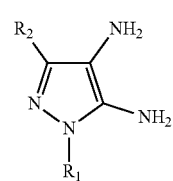

(I)

in which $R_1$ and $R_2$ independently of one another are hydrogen or a linear or branched C1-C10 alkyl group which may be substituted by one to ten hydroxyl groups, where $R_1$ and $R_2$ are not simultaneously hydrogen, is present in the dyes (A) as a developer component or oxidation base.

Oxidation dye precursors of structure (I) preferred as contemplated herein are those in which $R_1$ is a linear or branched C1-C10 alkyl group which may be substituted with one to ten hydroxyl groups and $R_2$ is hydrogen.

Particularly preferred as contemplated herein is the oxidation dye precursor of structure (I) in which $R_1$ is a 2-hydroxyethyl group and $R_2$ is hydrogen, i.e., 4,5-diamino-1-(2-hydroxyethyl)-1H-pyrazole and/or one of its physiologically tolerated salts, preferably 4,5-diamino-1-(2-hydroxyethyl)-1H-pyrazole sulfate.

Also highly preferred as contemplated herein is the oxidation dye precursor of structure (I), in which $R_1$ represents an n-hexyl group and $R_2$ represents hydrogen. Oxidative colorants containing this dye 4,5-diamino-1-hexylpyrazole are known, for example, from WO2016177344A1.

The developer component 4,5-diamino-1-(2-hydroxyethyl)-1H-pyrazole has long been used in many oxidation dyes. Corresponding agents are known, for example, from EP 1321131A2. This document teaches the use of an N-containing silicone, polystyrene sulfonate, and/or pyrrolidone to improve the wash fastness of oxidative hair dyes containing an oxidation dye precursor such as 4,5-diamino-1-(2-hydroxyethyl)-1H-pyrazole.

On the other hand, it is known that polymers, such as N-containing silicones or polystyrene sulfonate, can have a color-shifting influence on the coloration in the sense that a color shift of the coloration result occurs compared to the colorant base without the fastness-improving additive. Such color shifts are undesirable for technical and economic reasons.

Pyrrolidone forms flammable vapor-air mixtures above its flash point of 138° C. and is therefore a less preferred ingredient for large-scale manufacturing of a cosmetic product.

The technical task was thus to provide alternative oxidation dyes with 4,5-diaminopyrazoles as the developer component for red shades with high fastness to washing, whose fastness-enhancing additive causes no or only very slight color shifts, can be processed on an industrial scale without problems and is based on raw materials that are as ecologically harmless as possible.

Another technical task was to provide alternative oxidation dyes with 4,5-diaminopyrazoles as the developer component for red shades with high homogeneity or low selectivity of the dyeing along the entire hair fiber, whose homogeneity-improving additive causes no or only very slight color shifts, can be processed on a large scale without any problems and is based on raw materials that are as ecologically harmless as possible.

Surprisingly, it was found that with the combination of (A) at least one oxidation dye precursor with 4,5-diaminopyrazole as the basic structural element according to the structural formula (I) and furthermore (B) glucoheptonic acid and/or at least one of its physiologically compatible salts and/or lactones, oxidation colorants are obtained on a cosmetic carrier which provide attractive and fashionable red shades with high fastness to washing, are uncomplicated to prepare and are based on ecologically safe raw materials.

Oxidation colorants containing glucoheptonic acid or sodium glucoheptonate (INCI: sodium glucepate) are known in the prior art from WO 2006/106366A1 and WO 2003/015734A1, furthermore also from JP2004210700A. Corresponding market products are disclosed at Mintel® GNPD®, entry numbers 928580, 667942, 298707 and 28770. None of these documents disclose a content of 4,5-diaminopyrazoles or the use of glucoheptonic acid or sodium glucoheptonate to improve wash fastness.

A first object of the present disclosure is therefore an agent for oxidative dyeing of keratinous fibers, in particular human hair, comprising in a cosmetic carrier
(A) at least one oxidation dye precursor of structure (I) and/or one of its physiologically acceptable salts

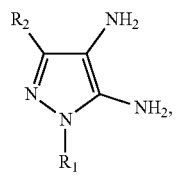

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore (B) glucoheptonic acid and/or at least one of its physiologically tolerated salts and/or lactones, and (C) at least one oxidizing agent other than atmospheric oxygen.

Keratinic fibers, keratin containing fibers or keratin fibers are to be understood as furs, wool, feathers, and in particular human hair. Although the agents as contemplated herein are primarily suitable for dyeing keratin fibers, in principle there is nothing to prevent their use in other fields as well.

The term "oxidative dyeing agents" as used in the present disclosure refers to oxidative dyeing agents containing developer-type and coupler-type oxidation dye products. The coloration is formed by the presence of an oxidizing agent (C) other than atmospheric oxygen, which is preferably hydrogen peroxide. Depending on the amount of oxidant used, the keratin fiber is simultaneously lightened to a greater or lesser extent during dyeing, since the oxidant not only initiates the dye formation process of developers and couplers, but also oxidatively destroys the hair's own pigments (melanins).

The compositions as contemplated herein contain the at least one oxidation dye precursor (A) of structure (I) as well as component (B) and the oxidizing agent (C) in a cosmetic carrier, preferably in a suitable aqueous, alcoholic, or aqueous-alcoholic carrier. To oxidative coloring, such carriers may be, for example, creams, emulsions, gels or even foaming solutions, such as shampoos, foam aerosols, foam formulations or other preparations suitable for application to the hair. Particularly preferred agents for oxidative dyeing of keratinous fibers are creams or emulsions.

A characteristic feature of the compositions as contemplated herein is a content of at least one oxidation dye precursor (A) of structure (I) and/or one of its physiologically tolerated salts

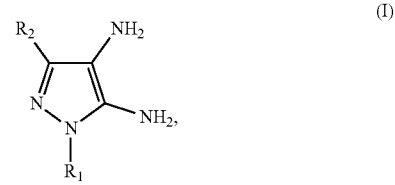

wherein $R_1$ and $R_2$ are independently hydrogen or a linear or branched $C_1$-$C_{10}$ alkyl group which may be substituted with one to ten hydroxyl groups, but $R_1$ and $R_2$ are not simultaneously hydrogen.

For the purposes of the present disclosure, a developer is understood to mean a developer-type oxidation dye precursor. For the purposes of the present disclosure, a coupler refers to a coupler-type oxidation dye precursor.

As oxidation dye precursor (A), extraordinarily preferred agents as contemplated herein contain 4,5-diamino-1-(2-hydroxyethyl)-1H-pyrazole and/or one of its physiologically tolerable salts.

4,5-Diamino-1-(2-hydroxyethyl)-1H-pyrazole is the compound of the formula (I-A), i.e., an oxidation dye precursor of structure (I), in which $R_1$ is a 2-hydroxyethyl group and $R_2$ is hydrogen, i.e., 4,5-diamino-1-(2-hydroxyethyl)-1H-pyrazole and/or one of its physiologically tolerated salts:

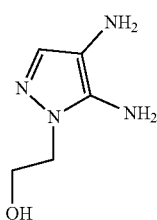

molar mass = 142.16 g/mol.

Preferred physiologically acceptable salts of 4,5-diamino-1-(2-hydroxyethyl)-1H-pyrazole are the hydrochlorides (monohydrochloride×HCl, or dihydrochloride×2 HCl), the sulfate (×H$_2$SO$_4$) and the hydrobromides (monohydrobromide×HBr, or dihydrobromide×2 HBr) of the compound. 4,5-diamino-1-(2-hydroxyethyl)-1H-pyrazole sulfate (formula (III)) is particularly preferred.

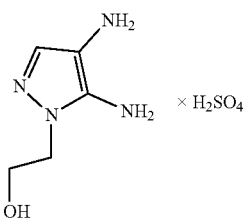

molar mass = 240.23 g/mol.

Further agents preferred as contemplated herein are exemplified in that they contain as oxidation dye precursor (A) at least one oxidation dye precursor of structure (I) in which R$_1$ is an n-hexyl group and R$_2$ is hydrogen (4,5-diamino-1-hexyl-1H-pyrazole).

Agents for oxidative dyeing preferred as contemplated herein are exemplified in that the at least one oxidation dye precursor (A) of structure (I) is present in a total amount of about 0.01 to about 2.5% by weight, preferably about 0.1 to about 1.8% by weight, particularly preferably about 0.2 to about 1.0% by weight, exceptionally preferably about 0.4 to about 0.9% by weight, the amounts being based on the weight of the free 4,5-diaminopyrazole base in relation to the weight of the agent as contemplated herein.

Agents for oxidative dyeing which are particularly preferred as contemplated herein are exemplified in that 4,5-diamino-1-(2-hydroxyethyl)-1H-pyrazole (structure I-A) is present in a total amount of about 0.01 to about 2.5% by weight, preferably from about 0.1 to about 1.8% by weight, particularly preferably from about 0.2 to about 1.0% by weight, particularly preferably from about 0.2 to about 1.0 wt. %, exceptionally preferably from about 0.4 to about 0.9 wt. %, the amounts being based on the weight of the free 4,5-diaminopyrazole base relative to the weight of the agent as contemplated herein.

4,5-Diamino-1-(2-hydroxyethyl)-1H-pyrazole (I-A) is very preferably used in the form of the sulfate salt in an amount of about 0.025 to about 4.5% by weight, preferably from about 0.1 to about 3.5% by weight, more preferably from about 0.2 to about 2.0% by weight and very particularly preferably from about 0.3 to about 1.0% by weight. Here, the amount given is based on the weight of 4,5-diamino-1-(2-hydroxyethyl)-1H-pyrazole sulfate (formula (III)), which is set in relation to the weight of the agent as contemplated herein.

In a particularly preferred embodiment, an agent as contemplated herein is exemplified in that it contains—based on its total weight—(A), about 0.025 to about 4.5% by weight, preferably from about 0.1 to about 3.5% by weight, further preferably from about 0.2 to about 2.0% by weight and very particularly preferably from about 0.3 to about 1.0% by weight of 4,5-diamino-1-(2-hydroxyethyl)-1H-pyrazole sulfate.

Further agents for oxidative dyeing preferred as contemplated herein are exemplified in that about 0.01 to about 2.5% by weight, preferably from about 0.1 to about 1.8% by weight, particularly preferably from about 0.2 to about 1.0% by weight, exceptionally preferably from about 0.4 to about 0.9% by weight of 4,5-diamino-1-hexyl-1H-pyrazole is present, the amounts being based on the weight of the free 4,5-diaminopyrazole base in relation to the weight of the agent as contemplated herein.

As a second essential ingredient (B), the compositions as contemplated herein contain glucoheptonic acid and/or at least one of its physiologically tolerable salts and/or lactones.

Glucoheptonic acid (226.18 g/mol) is also known as d-glycero-d-gulo heptonic acid.

Among the physiologically compatible salts of glucoheptonic acid used in the context of the present disclosure are the salts of alkali metals, alkaline earth metals and earth metals, especially lithium, sodium, potassium, magnesium, and calcium, particularly preferably sodium and potassium, exceptionally preferably sodium. Sodium glucoheptonate (INCI: sodium gluceptate; 248 g/mol), which is extremely preferred as contemplated herein, is commercially available.

Lactones of glucoheptonic acid preferred as contemplated herein include the 1,4-lactone (melting point 151° C.) and the 1,5-lactone, with the 1,4-lactone being exceptionally preferred.

Agents for oxidative dyeing preferred as contemplated herein are exemplified in that glucoheptonic acid and/or at least one of its physiologically compatible salts and/or lactones is/are present in a total amount of about 0.01 to about 2.5% by weight, preferably from about 0.05 to about 1.5% by weight, particularly preferably from about 0.1 to about 1.0% by weight, exceptionally preferably from about 0.1 to about 0.5% by weight, the amounts being based on the weight of free glucoheptonic acid in relation to the weight of the agent as contemplated herein.

As a third essential component, the agent for oxidative dyeing of keratinous fibers (C) as contemplated herein contains at least one oxidizing agent other than atmospheric oxygen.

Oxidizing agents (C) preferred as contemplated herein are selected from hydrogen peroxide, sodium percarbonate, percarbonates and persalts, peroxodisulfate salts and/or peroxomonosulfate salts, and mixtures thereof, hydrogen peroxide being particularly preferred as contemplated herein.

As soon as the at least one oxidation dye precursor (A) and optionally other contained oxidation dye precursors meet the oxidizing agent (C) in the presence of water, a coupling process starts, and dye formation begins.

Thus, the agent as contemplated herein containing ingredients (A), (B) and (C) is the oxidative colorant ready for use, provided that the oxidizing agent (C) comprises hydrogen peroxide.

Agents as contemplated herein which contain the ingredients (A), (B) and (C), wherein the oxidizing agent (C)

alone is selected from sodium percarbonate, percarbonates and persalts, peroxodisulfate salts and/or peroxomonosulfate salts, require a content of water to activate the oxidizing agent (C) and to start the coupling process of the oxidation dye precursors and the associated dye formation.

The amount of oxidizer will be chosen by the professional depending on the desired whitening performance. If the formation of a very dark red shade is desired, the specialist will reduce the amount of hydrogen peroxide used accordingly. However, if a bright shade of red is to be achieved on dark hair, the hair must also be lightened to a significant degree at the same time. In this case, the amount of hydrogen peroxide used is selected to be correspondingly high; if necessary, a persalt, one or more peroxodisulfate salts and/or peroxomonosulfate salts, such as potassium persulfate, sodium persulfate or ammonium persulfate, can be included as a further oxidizing agent (C) for this case.

Agents preferred as contemplated herein are exemplified in that they contain, in each case based on their weight, about 0.5 to about 12% by weight, preferably from about 0.9 to about 7% by weight, particularly preferably from about 1.5 to about 5% by weight, exceptionally preferably from about 3 to about 4.5% by weight hydrogen peroxide (calculated as 100% $H_2O_2$) as oxidizing agent (C).

In a further preferred embodiment, the compositions as contemplated herein contain sodium percarbonate as oxidizing agent (C). Sodium percarbonate (2 $Na_2CO_3 \cdot 3\ H_2O_2$) is an addition compound or adduct of hydrogen peroxide ($H_2O_2$) to sodium carbonate ($Na_2CO_3$). Agents with sodium percarbonate as oxidizing agent (C) preferred as contemplated herein, which are preferably initially anhydrous, release hydrogen peroxide when mixed with water, which causes the coupling process of the oxidation dye precursors with each other and the resulting dye formation.

Agents preferred as contemplated herein are therefore exemplified in that they contain, in each case based on their weight, about 0.5 to about 90% by weight, preferably from about 5 to about 85% by weight, particularly preferably from about 15 to about 80% by weight, exceptionally preferably from about 50 to about 75% by weight, of sodium percarbonate as oxidizing agent (C).

Other agents preferred as contemplated herein are exemplified in that they contain, in each case based on their weight, about 0.5 to about 90% by weight, preferably from about 5 to about 85% by weight, particularly preferably from about 15 to about 80% by weight, exceptionally preferably from about 50 to about 75% by weight of sodium percarbonate as oxidizing agent (C) and about 0 to about 10% by weight, preferably from about 0.1 to about 8% by weight, particularly preferably from about 0.5 to about 5% by weight of water.

These figures refer to the content of free water. Not considered is the content of molecularly bound water or water of crystallization that individual ingredients of this embodiment may have. The water content can be determined by Karl Fischer titration according to ISO 4317 (Version 2011-12).

In a further preferred embodiment, the compositions as contemplated herein contain as oxidizing agent (C) a combination of hydrogen peroxide and at least one persalt, one or more peroxodisulfate salts and/or peroxomonosulfate salts, such as potassium persulfate, sodium persulfate or ammonium persulfate.

Agents preferred as contemplated herein are therefore exemplified in that they contain, in each case based on their weight, about 0.5 to about 12% by weight, preferably from about 0.9 to about 7% by weight, particularly preferably from about 1.5 to about 5% by weight, exceptionally preferably from about 3 to about 4.5% by weight of hydrogen peroxide (calculated as 100% $H_2O_2$) and at least one persalt in a total amount of about 0.1 to about 20% by weight, preferably from about 1 to about 15% by weight, particularly preferably from about 3 to about 10% by weight, as oxidizing agent (C).

In the above-described composition as contemplated herein containing hydrogen peroxide as oxidizing agent (C), it is the composition ready for use which already contains both at least one oxidation dye precursor (A) and an oxidizing agent (C) which brings about the coupling process of the oxidation dye precursor(s) to one another and the accompanying dye formation, namely hydrogen peroxide. To prepare this ready-to-use colorant and to initiate the dye formation reaction, a first component K1 containing the at least one oxidation dye precursor (A) and optionally further oxidation dye precursors (ODP) but free from dissolved hydrogen peroxide is usually mixed with a second component K2 containing hydrogen peroxide as oxidizing agent (C). The obtained ready-to-use dye is intended for immediate application to the hair to be dyed. The at least one active ingredient (B) as contemplated herein, i.e., glucoheptonic acid and/or at least one of its physiologically tolerable salts and/or lactones, may be present in component K1 or in component K2. For the large-scale production of the components of an oxidation colorant, it may be preferable to formulate the hydrogen peroxide-containing component K2 in as little complex, standardized composition as possible, i.e., to provide the active ingredient (B) as contemplated herein, i.e., glucoheptonic acid and/or at least one of its physiologically tolerable salts and/or lactones, in the ODP-containing component K1.

To avoid incompatibilities and prevent premature, undesirable dye formation, components K1 (containing oxidation dye precursors) and K2 (oxidant preparation with dissolved hydrogen peroxide) are always packaged separately and brought into contact with each other only shortly before use. For the consumer, the components (K1) and (K2) are preferably provided in the form of a multi-component packaging unit (kit-of-parts).

A second object of the present disclosure is therefore a multi-component packaging unit (kit-of-parts) for oxidative dyeing of keratinous fibers, comprising at least two separately prepared components (K1) and (K2), wherein the first component (K1) in a cosmetic carrier (A) contains at least one oxidation dye precursor of the structure (I) and/or one of its physiologically tolerated salts

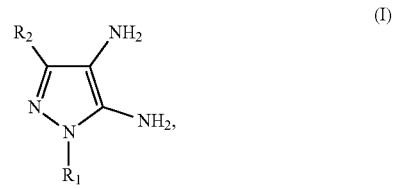

(I)

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore (C) optionally at least one oxidizing agent selected from persalts, peroxodisulfate salts and/or peroxomonosulfate salts, the second component (K2)

(C) contains hydrogen peroxide dissolved in water, exemplified in that at least one of the components (K1) or (K2)

(B) comprises glucoheptonic acid and/or at least one of its physiologically tolerated salts and/or lactones.

For the large-scale production of the components of an oxidation colorant, it may be preferable to formulate the hydrogen peroxide-containing component K2 in as little complex, standardized composition as possible, i.e., to provide the active ingredient (B) as contemplated herein, i.e., glucoheptonic acid and/or at least one of its physiologically tolerable salts and/or lactones, in the ODP-containing component K1.

Preferred as contemplated herein is therefore a multi-component packaging unit (kit-of-parts) for the oxidative dyeing of keratinous fibers, comprising at least two separately prepared components (K1) and (K2), wherein the first component (K1) in a cosmetic carrier (A) contains at least one oxidation dye precursor of the structure (I) and/or one of its physiologically tolerated salts

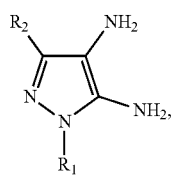

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore (B) contains glucoheptonic acid and/or at least one of its physiologically tolerated salts and/or lactones, furthermore (C) optionally contains at least one oxidizing agent selected from persalts, peroxodisulfate salts and/or peroxomonosulfate salts, the second component (K2)

(C) contains hydrogen peroxide dissolved in water.

What has been said with respect to preferred oxidation dye precursors (A) of structure (I), preferred qualitative embodiments of ingredient (B), and preferred qualitative embodiments of ingredient (C) with respect to the first subject matter of the present disclosure also applies mutatis mutandis to the second subject matter of the present disclosure. The preferred amounts of ingredients (A), (B) and (C) disclosed above for the first subject matter of the present disclosure as contemplated herein also apply mutatis mutandis to the mixtures of components (K1) and (K2) of the second subject matter of the present disclosure. The concentrations of the ingredients (A), (B) and (C) in the components (K1) and (K2) and the mixing ratios of the components (K1) and (K2) to each other are to be selected accordingly by the skilled person so that the mixtures of the components (K1) and (K2) have the preferred amounts of ingredients (A), (B) and (C) disclosed above for the first subject matter of the present disclosure.

A third object of the present disclosure is a multi-component packaging unit (kit-of-parts) for oxidative dyeing of keratinous fibers, comprising at least two separately prepared components (K1) and (K2), wherein the first component (K1) in a cosmetic carrier (A) contains at least one oxidation dye precursor of the structure (I) and/or one of its physiologically tolerated salts

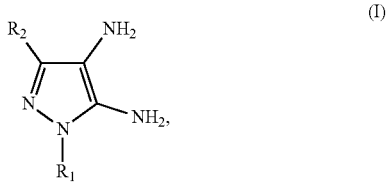

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore (C) contains sodium percarbonate as oxidizing agent and optionally at least one further oxidizing agent selected from persalts, peroxodisulfate salts and/or peroxomonosulfate salts, the second component (K2) contains water.

The kit-of-parts is exemplified in that at least one of the components (K1) or (K2)

(B) comprises glucoheptonic acid and/or at least one of its physiologically tolerated salts and/or lactones.

Also, for this third object of the present disclosure, it is preferred that the multi-component packaging unit (kit-of-parts) for oxidative dyeing of keratinous fibers comprises at least two separately prepared components (K1) and (K2), wherein the first component (K1) in a cosmetic carrier (A) contains at least one oxidation dye precursor of the structure (I) and/or one of its physiologically tolerated salts

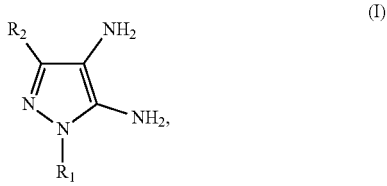

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore (B) contains glucoheptonic acid and/or at least one of its physiologically tolerated salts and/or lactones, and furthermore (C) contains sodium percarbonate as oxidizing agent and optionally at least one further oxidizing agent selected from persalts, peroxodisulfate salts and/or peroxomonosulfate salts, and the second component (K2) contains water.

What has been said with respect to preferred oxidation dye precursors (A) of structure (I), preferred qualitative embodiments of ingredient (B), and preferred qualitative embodiments of ingredient (C) with respect to the first subject matter of the present disclosure also applies mutatis mutandis to the third subject matter of the present disclosure. The preferred amounts of ingredients (A), (B) and (C) as contemplated herein disclosed above for the first subject matter of the present disclosure also apply mutatis mutandis to the mixtures of components (K1) and (K2) of the third subject matter of the present disclosure. The concentrations of the ingredients (A), (B) and (C) in the components (K1) and (K2) and the mixing ratios of the components (K1) and (K2) to each other are to be selected accordingly by the skilled person so that the mixtures of the components (K1) and (K2) have the preferred amounts of ingredients (A), (B) and (C) disclosed above for the first subject matter of the present disclosure.

A fourth object of the present disclosure is a multi-component packaging unit (kit-of-parts) for oxidative dyeing of keratinous fibers, comprising at least three separately prepared components (K1), (K2) and (K3), wherein the first component (K1) in a cosmetic carrier
(A) contains at least one oxidation dye precursor of the structure (I) and/or one of its physiologically tolerated salts

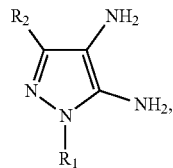

(I)

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore
(C) optionally contains at least one oxidizing agent selected from persalts, peroxodisulfate salts and/or peroxomonosulfate salts,
the second component (K2)
(C) contains hydrogen peroxide dissolved in water,
the third component (K3)
(B) contains glucoheptonic acid and/or at least one of its physiologically tolerated salts and/or lactones.

The fourth object of the present disclosure, as set forth above, provides that component (B), i.e., glucoheptonic acid and/or at least one of its physiologically acceptable salts and/or lactones, is contained separately from the ODP-containing component (K1) and separately from the hydrogen peroxide-containing component (K2) in a third component (K3). The ready-to-use agent according to this embodiment is obtained by mixing components (K1), (K2) and (K3) together. In principle, the third component (K3) may contain the active ingredient (B), i.e., at least one physiologically tolerated salt of glucoheptonic acid and/or a lactone of glucoheptonic acid, in particular the 1,4-lactone of glucoheptonic acid, in pure, undiluted form. Glucoheptonic acid itself is only available in aqueous solution, because when the aqueous solution is evaporated, the 1,4-lactone of glucoheptonic acid crystallizes out, which has a melting point of 151° C. Since the present disclosure essentially relates to a consumer product, it should be designed in such a way that a homogeneous mixture suitable for immediate application to the fibers to be dyed can be prepared from components (K1), (K2) and (K3) as quickly as possible and with little apparatus effort. Therefore, component (K3) preferably includes an aqueous solution of the active ingredient (B) used as contemplated herein, i.e., glucoheptonic acid and/or at least one of its physiologically tolerated salts and/or lactones, which solution may optionally contain further ingredients.

What has been said with respect to preferred oxidation dye precursors (A) of structure (I), preferred qualitative embodiments of ingredient (B), and preferred qualitative embodiments of ingredient (C) with respect to the first subject matter of the present disclosure also applies mutatis mutandis to the fourth subject matter of the present disclosure. The preferred amounts of ingredients (A), (B) and (C) disclosed above for the first subject matter of the present disclosure as contemplated herein also apply mutatis mutandis to the mixtures of components (K1), (K2) and (K3) of the fourth subject matter of the present disclosure. The concentrations of the ingredients (A), (B) and (C) in the components (K1), (K2) or (K3) and the mixing ratios of the components (K1), (K2) and (K3) to each other are to be selected accordingly by the skilled person so that the mixtures of the components (K1), (K2) and (K3) have the preferred amounts of ingredients (A), (B) and (C) disclosed above for the first subject matter of the present disclosure.

A fifth object of the present disclosure is a multi-component packaging unit (kit-of-parts) for oxidative dyeing of keratinous fibers, comprising at least three separately prepared components (K1), (K2) and (K3), wherein the first component (K1) in a cosmetic carrier
(A) contains at least one oxidation dye precursor of the structure (I) and/or one of its physiologically tolerated salts

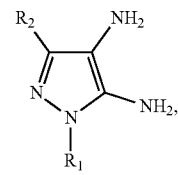

(I)

wherein $R_1$ and $R_2$ are independently hydrogen or a linear or branched C1-C10 alkyl group which may be substituted with one to ten hydroxyl groups, $R_1$ and $R_2$ not being hydrogen at the same time, furthermore
(C) contains sodium percarbonate as oxidizing agent and optionally at least one further oxidizing agent selected from persalts, peroxodisulfate salts and/or peroxomonosulfate salts,
the second component (K2) contains water,
the third component (K3)
(B) contains glucoheptonic acid and/or at least one of its physiologically tolerated salts and/or lactones.

The fifth object of the present disclosure set forth above provides that component (B), i.e., glucoheptonic acid and/or at least one of its physiologically acceptable salts and/or lactones, is contained separately from the ODP- and sodium percarbonate-containing component (K1) and separately from the water-containing component (K2) in a third component (K3). The ready-to-use agent according to this embodiment is obtained by mixing components (K1), (K2) and (K3) together. In principle, the third component (K3) may contain the active ingredient (B), i.e., at least one physiologically tolerated salt of glucoheptonic acid and/or a lactone of glucoheptonic acid, in particular the 1,4-lactone of glucoheptonic acid, in pure, undiluted form. Glucoheptonic acid itself is only available in aqueous solution, because when the aqueous solution is evaporated, the 1,4-lactone of glucoheptonic acid crystallizes out, which has a melting point of 151° C. Since the present disclosure essentially relates to a consumer product, it should be designed in such a way that a homogeneous mixture suitable for immediate application to the fibers to be dyed can be prepared from components (K1), (K2) and (K3) as quickly as possible and with little apparatus effort. Therefore, component (K3) preferably includes an aqueous solution of the active ingredient (B) used as contemplated herein, i.e., glucoheptonic acid and/or at least one of its physiologically tolerated salts and/or lactones, which solution may optionally contain further ingredients.

What has been said with respect to preferred oxidation dye precursors (A) of structure (I), preferred qualitative embodiments of ingredient (B), and preferred qualitative embodiments of ingredient (C) for the first subject matter of the present disclosure also applies mutatis mutandis to the fifth subject matter of the present disclosure. The preferred amounts of ingredients (A), (B) and (C) disclosed above for the first subject matter of the present disclosure as contemplated herein also apply mutatis mutandis to the mixtures of components (K1), (K2) and (K3) of the fifth subject matter of the present disclosure. The concentrations of the ingredients (A), (B) and (C) in the components (K1), (K2) or (K3) and the mixing ratios of the components (K1), (K2) and (K3) to each other are to be selected accordingly by the skilled person so that the mixtures of the components (K1), (K2) and (K3) have the preferred amounts of ingredients (A), (B) and (C) disclosed above for the first subject matter of the present disclosure n.

The first component of the second, third, fourth and fifth subject matter of the present disclosure is the—preferably alkaline adjusted—dyeing preparation (K1) which contains the at least one oxidation dye precursor (A) of structure (I) as well as optionally additional oxidation dye precursors and/or further direct dyes.

Before use, this staining preparation is mixed with an oxidizing agent preparation (K2). For stability reasons, the oxidant preparation (K2) is preferably adjusted to an acidic pH and contains the oxidizing agent. The oxidant preparation (K2) of the first, second and fourth objects of the present disclosure is hydrogen peroxide used in the form of an aqueous solution.

Components (K1) and (K2) can be mixed in different weight ratios (K1)/(K2) of, for example, from about 0.3 to about 3.0, preferably from about 0.5 to about 2.5, particularly preferably from about 0.45 to about 1.5, and exceptionally preferably in a weight ratio of about 1:1.

A particularly preferred process for oxidative hair dyeing is therefore exemplified in that the first component (K1) and the second component (K2) are mixed with one another in a weight ratio (K1)/(K2) of about 0.3 to about 3.0, preferably of about 0.45 to about 2.5, particularly preferably of about 0.45 to about 1.5 and exceptionally preferably in a weight ratio of about 1:1.

The cosmetic carrier for component (K1), which contains the at least one oxidation dye precursor (A) with 4,5-diaminopyrazole as the basic structural element according to the structural formula (I) until the preparation of the ready-to-use colorant, may be formulated as a water-based emulsion, a spray, a cream, a gel, a lotion, a paste, or a shampoo.

Further preferred oxidation colorants as contemplated herein are exemplified in that they contain at least one linear saturated alkanol having 12-30 carbon atoms. For the purposes of the present disclosure, alkanols with at least 8 carbon atoms are considered fatty substances, not surfactants.

Preferred linear saturated alkanols having 12-30 carbon atoms, especially 16-22 carbon atoms, are selected from cetyl alcohol, stearyl alcohol, arachidyl alcohol, behenyl alcohol and lanolin alcohol, and mixtures of these alkanols. Alkanol mixtures particularly preferred as contemplated herein are those obtainable in the technical hydrogenation of vegetable and animal fatty acids. Preferably, the total amount of at least one linear saturated alkanol having 12-30 carbon atoms in the oxidation colorant as contemplated herein is about 0.1-about 20% by weight, preferably from about 0.5-about 16.5% by weight and particularly preferably from about 3-about 10% by weight, in each case based on the weight of the oxidation colorant ready for use. Further preferably, the total amount of at least one linear saturated alkanol having 12-30 carbon atoms in the ODP-containing component (K1) of the oxidation colorant as contemplated herein is about 0.1-20% by weight, preferably from about 0.5-about 16.5% by weight, and particularly preferably from about 3-about 10% by weight, in each case based on the weight of the component (K1) of the oxidation colorant as contemplated herein.

Further preferred oxidation colorants as contemplated herein contain at least one surfactant or emulsifier.

For the purposes of the present application, surfactants and emulsifiers are amphiphilic (bifunctional) compounds which include at least one hydrophobic and at least one hydrophilic part of the molecule. The hydrophobic radical is preferably a hydrocarbon chain with 8-28 carbon atoms, which can be saturated or unsaturated, linear, or branched. This $C_8$-$C_{28}$ alkyl chain is particularly preferably linear. Basic properties of surfactants and emulsifiers are the oriented absorption at interfaces as well as the aggregation to micelles and the formation of lyotropic phases.

When selecting surfactants suitable as contemplated herein, it may be preferable to use a mixture of surfactants to optimally adjust the stability of the oxidation colorants as contemplated herein.

Preferably, the total amount of at least one surfactant in the oxidation colorants as contemplated herein is about 0.1-about 20% by weight, preferably from about 0.5-about 10% by weight and particularly preferably from about 1.5-about 5% by weight, in each case based on the weight of the oxidation colorant ready for use.

Further preferably, the total amount of at least one surfactant in the ODP-containing component (K1) of the oxidation colorant as contemplated herein is about 0.1-about 20% by weight, preferably from about 0.5-about 10% by weight and particularly preferably from about 1.5-about 5% by weight, in each case based on the weight of the component (K1) of the oxidation colorant as contemplated herein.

Preferred surfactants and emulsifiers are selected from anionic, cationic, zwitterionic, amphoteric and nonionic surfactants and emulsifiers and mixtures thereof. These substances are described below.

Preferred oxidation colorants as contemplated herein are exemplified in that the at least one surfactant present is selected from nonionic surfactants and anionic surfactants and mixtures thereof. Further preferred oxidation colorants as contemplated herein are exemplified in that their ODP-containing component (K1) comprises at least one surfactant selected from nonionic surfactants and anionic surfactants and mixtures thereof.

Suitable anionic surfactants are all anionic surface-active substances suitable for use on the human body which have a water-solubilizing anionic group, for example a carboxylate, sulfate, sulfonate or phosphate group, and a lipophilic alkyl group with about 8 to 30 C atoms, preferably 8 to 24

C atoms, in the molecule. In addition, glycol or polyglycol ether groups, ester, ether and amide and hydroxyl groups may also be present in the molecule. Examples of suitable anionic surfactants are, in each case in the form of the sodium, potassium and ammonium as well as the mono, di and trialkanolammonium salts with 2 to 4 C atoms in the alkanol group, linear and branched fatty acids with 8 to 30 C atoms (soaps), polyethoxylated ether carboxylic acids, acyl sarcosides, acyl taurides, acyl isethionates, sulfosuccinic acid mono- and dialkyl esters and sulfosuccinic acid mono-alkyl polyoxyethyl esters containing 1 to 6 ethylene oxide groups, linear alkane sulfonates, linear alpha-olefin sulfonates, sulfonates of unsaturated fatty acids with up to 6 double bonds, alpha-sulfofatty acid methyl esters of fatty acids, $C_8$-$C_{20}$ alkyl sulfates and $C_8$-$C_{20}$ alkyl ether sulfates with up to about 15 oxyethyl groups, mixtures of surface-active hydroxysulfonates, sulfated hydroxyalkyl polyethylene and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, and monoglyceride sulfates and monoglyceride ether sulfates. Preferred anionic surfactants are soaps, $C_8$-$C_{20}$ alkyl sulfates, $C_8$-$C_{20}$ alkyl ether sulfates and $C_8$-$C_{20}$ ether carboxylic acids with 8 to 20 C atoms in the alkyl group and up to about 12 ethylene oxide groups in the molecule. Sodium cetearyl sulfate is particularly preferred.

Preferably, the total amount of at least one anionic surfactant in the oxidation colorants as contemplated herein is about 0.01-about 10% by weight, preferably from about 0.1-about 5% by weight and particularly preferably from about 1-about 3% by weight, in each case based on the weight of the oxidation colorant ready for use.

Further preferably, the total amount of at least one anionic surfactant in the ODP-containing component (K1) of the oxidation colorant as contemplated herein is about 0.01-about 10% by weight, preferably from about 0.1-about 5% by weight and particularly preferably from about 1-about 3% by weight, in each case based on the weight of the component (K1) of the oxidation colorant as contemplated herein.

Non-ionic surfactants used with particular preference are selected from about 20-100 moles of ethylene oxide per mole of ethoxylated castor oil, ethoxylated $C_8$-$C_{24}$ alkanols with about 1-200 moles of ethylene oxide per mole, ethoxylated $C_8$-$C_{24}$ carboxylic acids with about 1-200 moles of ethylene oxide per mole, with about 4-80 moles of ethylene oxide per mole of ethoxylated sorbitan monoesters of linear saturated and unsaturated $C_{12}$-$C_{30}$ carboxylic acids, which can be hydroxylated, especially those of myristic acid, palmitic acid, stearic acid or of mixtures of these fatty acids, alkyl mono- and oligoglycosides with 8 to 22 carbon atoms in the alkyl radical and their ethoxylated analogues, and mixtures of the aforementioned substances.

The ethoxylated $C_8$-$C_{24}$ alkanols have the formula $R^1O(CH_2CH_2O)_nH$, where $R^1$ is a linear or branched alkyl and/or alkenyl radical containing 8-24 carbon atoms and n, the average number of ethylene oxide units per molecule, for numbers from about 1-200, preferably about 2-150, particularly preferably about 4 to 100, exceptionally preferably about 10-50, further exceptionally preferred about 12-30 or about 20 moles of ethylene oxide to 1 mole of caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and their technical mixtures. Also adducts of about 1-200 moles of ethylene oxide with technical fatty alcohols with 12-18 carbon atoms, such as coconut, palm, palm kernel or tallow fatty alcohol, are also suitable. Particularly preferred are laureth-2, laureth-4, laureth-10, laureth-12, laureth-15, laureth-20, laureth-30, myreth-2, myreth-4, myreth-10, myreth-12, myreth-15, myreth-20, myreth-30, ceteth-2, Ceteth-4, Ceteth-10, Ceteth-12, Ceteth-15, Ceteth-20, Ceteth-30, Ceteth-50, Ceteth-100, Ceteth-150, Steareth-2, Steareth-4, Steareth-10, Steareth-12 Steareth-15, Steareth-20, Steareth-30, Steareth-50, Steareth-100, Steareth-150, Oleth-2, Oleth-4, Oleth-10, Oleth-12, Oleth-15, Oleth-20, Oleth-30, Ceteareth-2, Ceteareth-4, Ceteareth-10, Ceteareth-15, Ceteareth-12, Ceteareth-15, Ceteareth-20, Ceteareth-30, Ceteareth-50, Ceteareth-100, Ceteareth-150, and Coceth-2, Coceth-4, Coceth-10, Coceth-12, Coceth-15, Coceth-20, Coceth-30 Coceth-50 and Coceth-100.

The ethoxylated $C_8$-$C_{24}$ carboxylic acids have the formula $R^1O(CH_2CH_2O)_nH$, where $R^1O$ is a linear or branched saturated or unsaturated acyl radical containing 8-24 carbon atoms and n, the average number of ethylene oxide units per molecule, for numbers from about 1-200, preferably about 10-50 moles ethylene oxide to 1 mole caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachyic acid, gadoleic acid, behenic acid, erucic acid and brassidic acid and their technical mixtures. Adducts of about 1-200, preferably about 10-50 moles ethylene oxide to technical fatty acids with 12-18 carbon atoms, such as coconut, palm, palm kernel or tallow fatty acids, are also suitable. Especially preferred are PEG-50-monostearate, PEG-100-monostearate, PEG-50-monooleate, PEG-100-monooleate, PEG-50-monolaurate and PEG-100-monolaurate.

Preferred sorbitan monoesters of linear saturated and unsaturated $C_{12}$-$C_{30}$ carboxylic acids ethoxylated with about 4-80 moles of ethylene oxide per mole, which may be hydroxylated, are selected from polysorbate-20, polysorbate-40, polysorbate-60, and polysorbate-80.

Other preferred nonionic surfactants are selected from $C_8$-$C_{22}$ alkyl mono- and oligoglycosides. $C_8$-$C_{22}$ alkyl mono- and oligoglycosides represent well-known, commercially available surfactants and emulsifiers. They are produced by reacting glucose or oligosaccharides with primary alcohols containing 8-22 carbon atoms. About the glycoside residue, monoglycosides in which a cyclic sugar residue is glycosidically bonded to the fatty alcohol as well as oligomeric glycosides with a degree of oligomerization of up to about 8, preferably 1-2, are suitable. The degree of oligomerization is a statistical mean value based on a homologue distribution that is common for such technical products. Products available under the trademark Plantacare® contain a glucosidically bonded $C_8$-$C_{16}$ alkyl group on an oligoglucoside residue whose average degree of oligomerization is 1-2, 1.2-1.4. Particularly preferred $C_8$-$C_{22}$ alkyl mono- and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Glucamine-derived acylglucamides are also suitable as non-ionic oil-in-water emulsifiers.

Other nonionic surfactants suitable as contemplated herein contain, for example, a polyol group, a polyalkylene glycol ether group or a combination of polyol and polyglycol ether group as the hydrophilic group. Such links include Polyglycerol esters and ethoxylated polyglycerol esters of C8-C30 fatty acids, such as poly(3)glycerol diisostearate (commercial product: Lameform®TGI (BASF®)) and poly(2)glycerol polyhydroxystearate (commercial product: Dehymuls®PGPH (BASF®)), ethoxylated mono-, di- and triesters of glycerol with C8-C30 fatty acids, such as glycerol monolaurate+20 ethylene oxide and glycerol monostearate+20 ethylene oxide, PEG-x Castor Oil with degree of ethoxylation x=1-80 or PEG-x Hydrogenated Castor Oil with degree of ethoxylation x=1-80, Aminoxides of C8-C30 fatty amines, Sugar fatty acid esters and addition products of ethylene oxide to sugar fatty acid esters, e.g., sucrose stearate, methyl glucose sesquistearate, PEG-20 methyl glucose sesquistearate or PEG-120 methyl glucose dioleate, Addition products of ethylene oxide to fatty acid alkanolamides and fatty amines, fatty acid-N-alkylglucamides, monoesters of $C_8$-$C_{30}$ fatty acids and ethylene glycol, and Monoesters and diesters of $C_8$-$C_{30}$ fatty acids and glycerol, e.g., glycerol monostearate or glycerol distearate.

Oxidation colorants preferred as contemplated herein are therefore exemplified in that they contain at least one nonionic surfactant selected from castor oil ethoxylated with about 20-100 moles of ethylene oxide per mole, ethoxylated $C_8$-$C_{24}$ alkanols with about 1-200 moles of ethylene oxide per mole, ethoxylated $C_8$-$C_{24}$ carboxylic acids with about 1-200 moles ethylene oxide per mole, with about 4-80 moles ethylene oxide per mole ethoxylated sorbitan monoesters of linear saturated and unsaturated $C_{12}$-$C_{30}$ carboxylic acids which may be hydroxylated, in particular those of myristic acid, palmitic acid, stearic acid or of mixtures of these fatty acids, alkyl mono- and oligoglycosides with 8 to 22 carbon atoms in the alkyl radical and their ethoxylated analogues, acyl glucamides derived from glucamine, polyglycerol esters and ethoxylated polyglycerol esters of C8-C30 fatty acids, ethoxylated mono-, di- and triesters of glycerol with C8-C30 fatty acids, amine oxides of C8-C30 fatty amines, sugar fatty acid esters and adducts of ethylene oxide with sugar fatty acid esters, adducts of ethylene oxide with fatty acid alkanolamides and fatty amines, fatty acid N-alkyl glucamides, monoesters of $C_8$-$C_{30}$ fatty acids and ethylene glycol, monoesters and diesters of $C_8$-$C_{30}$ fatty acids and glycerol, and mixtures of the above substances.

Preferably, the total amount of at least one nonionic surfactant in the oxidation colorants as contemplated herein is about 0.01-about 15% by weight, preferably from about 0.1-about 10% by weight and particularly preferably from about 1-about 6% by weight, in each case based on the weight of the oxidation colorant ready for use.

In another preferred embodiment, the total amount of at least one nonionic surfactant in the ODP-containing component (K1) of the oxidation colorant as contemplated herein is about 0.01-about 15% by weight, preferably from about 0.1-about 10% by weight, and particularly preferably from about 1-about 6% by weight, in each case based on the weight of the component (K1) of the oxidation colorant as contemplated herein.

In another preferred embodiment, the total amount of at least one nonionic surfactant in the oxidant-containing component (K2) of the oxidation colorant as contemplated herein is about 0.01-about 15% by weight, preferably from about 0.1-about 10% by weight and particularly preferably from about 1-about 4% by weight, in each case based on the weight of the component (K2) of the oxidation colorant as contemplated herein.

In another preferred embodiment, the oxidation colorant as contemplated herein contains a total of about 0.1 to about 15% by weight, preferably from about 0.5 to about 10% by weight and particularly preferably from about 1-about 5% by weight, in each case based on the weight of the oxidation colorant ready for use, of a mixture of nonionic and anionic surfactants.

In another preferred embodiment, the ODP-containing component (K1) of the oxidation colorant as contemplated herein contains a total of about 0.1 to about 15% by weight, preferably from about 0.5 to about 10% by weight and particularly preferably about 1-about 5% by weight, in each case based on the weight of component (K1), of a mixture of nonionic and anionic surfactants.

In another preferred embodiment, the oxidant-containing component (K2) of the oxidation colorant as contemplated herein contains a total of about 0.1 to about 15% by weight, preferably from about 0.5 to about 10% by weight and particularly preferably from about 1-about 5% by weight, in each case based on the weight of component (K2), of a mixture of nonionic and anionic surfactants.

Zwitterionic surfactants are surface-active compounds which carry at least one quaternary ammonium group and at least one carboxylate, sulphonate or sulphate group in the molecule. Particularly suitable zwitterionic surfactants are the so-called betaines such as the N-alkyl-N,N-dimethylammonium glycinates, for example cocoalkyl dimethylammonium glycinate, N-acyl-aminopropyl-N,N-dimethylammonium glycinate, for example cocoacylaminopropyl dimethylammonium glycinate, and 2-alkyl-3-carboxymethyl-3-hydroxyethyl imidazolines each having 8 to 18 carbon atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Amphoteric surfactants are surface-active compounds which, apart from a $C_8$-$C_{24}$ alkyl or acyl group, contain at least one free amino group and at least one —COOH or —SO$_3$H group in the molecule and can form internal salts. Examples of suitable amphoteric surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having about 8 to 24 carbon atoms in the alkyl group. Particularly preferred amphoteric surfactants are N-Cocoalkylaminopropionate, Cocoacylaminoethylaminopropionate and $C_{12}$-$C_{18}$ Acylsarcosine.

In a further preferred embodiment, the oxidation colorant as contemplated herein contains a total of about 0.1 to about 10% by weight, preferably about 0.2 to about 6% by weight and particularly preferably from about 1-about 2% by weight, in each case based on the weight of the oxidation colorant ready for use, of at least one zwitterionic or/and one amphoteric surfactant.

In another preferred embodiment, the ODP-containing component (K1) of the oxidation colorant as contemplated herein contains a total of about 0.1 to about 10% by weight, preferably from about 0.2 to about 6% by weight and particularly preferably from about 1-about 4% by weight, in each case based on the weight of component (K1), of at least one zwitterionic or/and one amphoteric surfactant.

Optionally, the oxidation colorant as contemplated herein contains, based on its weight, at least one cosmetic oil in a total amount of about 0.01-about 10% by weight, preferably from about 0.1-about 5% by weight, particularly preferably from about 0.5-about 4% by weight, exceptionally preferably from about 1-about 2% by weight. In another preferred embodiment, the ODP-containing component (K1) of the oxidation colorant as contemplated herein contains a total of about 0.1 to about 10% by weight, preferably from about 0.2 to about 6% by weight and particularly preferably from about 1-about 4% by weight, in each case based on the weight of component (K1), of at least one cosmetic oil. In another preferred embodiment, the oxidant-containing component (K2) of the oxidation colorant as contemplated herein contains a total of about 0.1 to about 10% by weight, preferably from about 0.2 to about 6% by weight and particularly preferably from about 1-about 4% by weight, in each case based on the weight of component (K2), of at least one cosmetic oil. The cosmetic oil is liquid under normal conditions (20° C., 1013.25 mbar); essential oils and perfume oils or fragrances are not counted as cosmetic oils. Cosmetic oils which are liquid under normal conditions are not miscible with water. As contemplated herein, essential oils are mixtures of volatile components produced by steam distillation from vegetable raw materials, e.g., citrus oils. In so far as the present application refers to a cosmetic oil, it is always a cosmetic oil which is neither a perfume nor an essential oil, is liquid under normal conditions and is not miscible with water.

The definition of a fragrance within the meaning of the present notification is in line with the usual professional definition as it can be found in the RÖMPP Chemie Lexikon, December 2007. According to this, a fragrance is a chemical compound with smell and/or taste that excites the receptors of the hair cells of the olfactory system (adequate stimulus). The physical and chemical properties required for this are a low molar mass of maximum 300 g/mol, a high vapor pressure, minimal water, and high lipid solubility as well as weak polarity and the presence of at least one osmophoric group in the molecule. To distinguish volatile, low-molecular substances which are normally, and also for the purposes of the present application, not considered and used as perfume but primarily as solvents, such as ethanol, propanol, isopropanol and acetone, from perfumes of the present disclosure, perfumes of the present disclosure have a molecular weight of 74 to 300 g/mol, contain at least one osmophoric group in the molecule and have an odor and/or taste, that is to say, they excite the receptors of the hair cells of the olfactory system.

Oils which are particularly preferred as contemplated herein are selected from the esters of linear or branched saturated or unsaturated fatty alcohols having 2 to 30 carbon atoms with linear or branched saturated or unsaturated fatty acids having 2 to 30 carbon atoms, which may be hydroxylated. These include cetyl-2-ethylhexanoate, 2-hexyldecyl stearate, 2-hexyldecyl laurate, isodecyl neopentanoate, isononyl isononanoate, 2-ethylhexyl palmitate and 2-ethylhexyl stearate. Also preferred are isopropyl myristate, isopropyl palmitate, isopropyl stearate, isopropyl isostearate, isopropyl oleate, isooctyl stearate, Isononylstearate, isocetyl stearate, isononyl isononanoate, isotridecyl isononanoate, cetearyl isononanoate, 2-Ethylhexyl laurate, 2-ethylhexyl isostearate, 2-ethylhexyl cocoate, 2-octyldodecyl palmitate, butyl octanoic acid-2-butyl octanoate, Diisotridecylacetate, n-Butyl stearate, n-Hexyl laurate, n-Decyl oleate, oleyl oleate, oleylerucate, erucyl oleate, erucylerucate, ethylene glycol dioleate and ethylene glycol dipalmitate.

Further oils preferred as contemplated herein are selected from natural and synthetic hydrocarbons, particularly preferably from mineral oils, paraffin oils, $C_{18}$-$C_{30}$ isoparaffins, in particular isoeicosane, polyisobutenes and polydecenes, which are known, for example, under the name Emery® 3004, 3006, 3010 or under the name Ethylflo® from Albemarle® or Nexbase® 2004G and are available from Nestle®, further selected from $C_8$-$C_{16}$ isoparaffins, in particular from isodecane, isododecane, isotetradecane and isohexadecane and mixtures thereof, and 1,3-di-(2-ethylhexyl) cyclohexane.

Further oils preferred as contemplated herein are selected from the benzoic acid esters of linear or branched C8-22 alkanols. C12-C15-alkyl benzoate, isostearyl benzoate, ethylhexyl benzoate and octyl docecyl benzoate are particularly preferred.

Other preferred oils as contemplated herein are selected from fatty alcohols with 6-30 carbon atoms, which are unsaturated or branched and saturated or branched and unsaturated. The branched alcohols are often referred to as Guerbet alcohols because they are available after the Guerbet reaction. Preferred alcohol oils are 2-hexyldecanol, 2-octyldodecanol, 2-ethylhexyl alcohol and isostearyl alcohol.

Further preferred oils are selected from mixtures of Guerbet alcohols and Guerbet alcohol esters, e.g., mixtures of 2-Hexyldecanol and 2-Hexyldecyl laurate.

Further cosmetic oils preferred as contemplated herein are selected from the triglyceride's (=triple esters of glycerol) of linear or branched, saturated or unsaturated, optionally hydroxylated C8-30 fatty acids. The use of natural oils, e g Amaranth seed oil, apricot kernel oil, argan oil, avocado oil, babassu oil, cottonseed oil, borage seed oil, camelina oil, safflower oil, peanut oil, pomegranate seed oil, grapefruit seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soybean oil, sunshine flower oil, grape seed oil, walnut oil, wild rose oil, wheat germ oil, and the liquid components of coconut oil and the like. However, synthetic triglyceride oils, in particular capric/caprylic triglycerides, e.g., the commercial products Myritol® 318 or Myritol® 331 (BASF®) with unbranched fatty acid residues and glyceryltriisostearin with branched fatty acid residues are also preferred.

Further cosmetic oils which are particularly preferred as contemplated herein are selected from the dicarboxylic acid esters of linear or branched C2-C10 alkanols, diisopropyl adipate, di-n-butyl adipate, di-(2-ethylhexyl) adipate, dioctyl adipate, diethyl/di-n-butyl/Dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further preferred cosmetic oils as contemplated herein are selected from the adducts of 1 to 5 propylene oxide units with mono- or polyvalent C8-22 alkanols, such as octanol, decanol, decanediol, lauryl alcohol, myristyl alcohol and stearyl alcohol, e.g., B. PPG-2 myristyl ether and PPG-3 myristyl ether.

Other cosmetic oils preferred as contemplated herein are selected from the addition products of at least 6 ethylene oxide and/or propylene oxide units to mono- or polyvalent C3-22 alkanols such as glycerol, butanol, butanediol, myristyl alcohol and stearyl alcohol, which may be esterified if desired, e.g., PPG-14-butyl ether, PPG-9-butyl ether, PPG-10-butanediol, PPG-15-stearyl ether and glycereth-7-diisononanoate.

Further preferred cosmetic oils as contemplated herein are selected from the C8-C22 fatty alcohol esters of monovalent or polyvalent C2-C7 hydroxycarboxylic acids, in particular the esters of glycolic acid, lactic acid, malic acid, tartaric acid, citric acid, and salicylic acid.

Further cosmetic oils preferred as contemplated herein are selected from the symmetrical, asymmetrical, or cyclic esters of carbonic acid with $C_{3-22}$ alkanols, $C_{3-22}$ alkanediols or $C_{3-22}$ alkanetriols, e.g., B. dicaprylyl carbonate or the esters according to the teaching of DE 19756454 A1, glycerol carbonate.

Further cosmetic oils, which may be preferred as contemplated herein, are selected from the esters of dimers of unsaturated $C_{12}$-$C_{22}$ fatty acids (dimer fatty acids) with monovalent linear, branched, or cyclic $C_2$-$C_{18}$ alkanols or with polyvalent linear or branched $C_2$-$C_6$ alkanols.

Further cosmetic oils which are suitable as contemplated herein are selected from the silicone oils, to which e.g., Dialkyl- and alkylarylsiloxanes, such as cyclopentasiloxane, cyclohexasiloxane, dimethylpolysiloxane and methylphenylpolysiloxane, but also hexamethyldisiloxane, octamethyltrisiloxane and decamethyltetrasiloxane count. Preferred can be volatile silicone oils, which can be cyclic, such as octamethylcyclotetrasiloxane, decamethylcyclopentasiloxane and dodecamethylcyclohexasiloxane, as well as mixtures thereof, as described, for. B. are contained in the commercial products DC 244, 245, 344 and 345 from Dow Corning®. Also suitable are volatile linear silicone oils, hexamethyldisiloxane ($L_2$), Octamethyltrisiloxane ($L_3$), Decamethyltetrasiloxane ($L_4$) and any two- and three-component mixtures of $L_2$, $L_3$ and/or $L_4$, preferably mixtures such as those described, for. B. in the commercial products DC 2-1184, Dow Corning® 200 (0.65 cSt) and Dow Corning® 200 (1.5 cSt) from Dow Corning®. Preferred non-volatile silicone fluids are selected from higher molecular weight linear dimethylpolysiloxanes, commercially available, for example, under the name Dow Corning® 190, Dow Corning® 200 Fluid with kinematic viscosities (25° C.) in the range of 5-100 cSt, preferably 5-50 cSt or even 5-10 cSt, and dimethylpolysiloxane with a kinematic viscosity (25° C.) of about 350 cSt.

As contemplated herein, it can be extremely preferred to use mixtures of the oils.

Preferred colorants as contemplated herein are exemplified in that the cosmetic oil is selected from natural and synthetic hydrocarbons, particularly preferably kerosene oils, $C_{18}$-$C_{30}$ isoparaffins, especially isoeicosane, polyisobutenes and polydecenes, $C_8$-$C_{16}$ isoparaffins, and 1,3-di-(2-ethylhexyl)-cyclohexane; the benzoic esters of linear or branched $C_{8-22}$ alkanols; fatty alcohols containing 6-30 carbon atoms that are unsaturated or branched and saturated or branched and unsaturated; triglycerides of linear or branched, saturated or unsaturated, optionally hydroxylated $C_{8-30}$ fatty acids, in particular natural oils; the dicarboxylic esters of linear or branched $C_2$-$C_{10}$ alkanols; the esters of linear or branched saturated or unsaturated fatty alcohols having 2-30 carbon atoms with linear or branched, saturated or unsaturated fatty acids having 2-30 carbon atoms, which may be hydroxylated; the addition products of 1 to 5 propylene oxide units to monovalent or polyvalent $C_{8-22}$ alkanols; the addition products of at least 6 ethylene oxide and/or propylene oxide units to monovalent or polyvalent $C_{3-22}$ alkanols; the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ is alkanols or with polyvalent linear or branched $C_2$-$C_6$ alkanols; silicone oils and mixtures of the above-mentioned substances.

In addition, the multi-component packaging units as contemplated herein may also contain one or more further separately assembled components. This or these additional separately prepared components may be, for example, a pre-treatment agent or an aftertreatment agent, such as shampoos or conditioners.

To ensure adequate swelling of the keratin fibers, the oxidative colorant ready for use is preferably adjusted to an alkaline pH value. The staining processes on keratin fibers also usually take place in an alkaline environment. To protect the keratin fibers and the skin as much as possible, the adjustment of a too high pH-value is however not desirable. Therefore, it is preferred if the pH of the ready-to-use agent is from about 8.0 to about 10.5, more preferably from about 8.7 to about 10.3, still more preferably from about 9.0 to about 10.2, and especially preferably from about 9.2 to about 10.1. The pH values given are values measured at a temperature of 22° C. with a glass electrode.

The alkalizing agents required to adjust the alkaline pH are usually contained in component (K1) together with the at least one oxidation dye precursor. The alkalizing agents usable as contemplated herein can be selected from the group formed by ammonia, alkanolamines, basic amino acids, as well as inorganic alkalizing agents such as (earth) alkali metal hydroxides, (earth) alkali metal metasilicates, (earth) alkali metal phosphates and (earth) alkali metal hydrogen phosphates. Preferred inorganic alkalizing agents are sodium hydroxide, potassium hydroxide, sodium silicate and sodium metasilicate. The alkanolamines which can be used as alkalizing agents are preferably selected from primary amines with a $C_2$-$C_6$ alkyl base body which carries at least one hydroxyl group. Particularly preferred alkanolamines are selected from the group formed by 2-amino-ethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, and 2-amino-2-methylpropane-1,3-diol. Alkanolamines which are particularly preferred as contemplated herein are selected from the group including 2-aminoethan-1-ol, 2-amino-2-methylpropan-1-ol and 2-amino-2-methylpropane-1,3-diol. The basic amino acids which can be used as alkalizing agents as contemplated herein are preferably selected from the group formed by arginine, lysine, ornithine, and histidine, particularly preferably arginine. However, during the examination of the present disclosure it turned out that, as contemplated herein, preferred agents are still exemplified by the fact that they additionally contain an organic alkalizing agent. One embodiment of the first subject matter of the present disclosure is exemplified in that the composition additionally contains at least one alkalizing agent selected from the group formed by ammonia, alkanolamines and basic amino acids, in particular ammonia, monoethanolamine and arginine or its compatible salts. Preferably, the alkalizing agent(s) are present in the dye preparation (K1) together with the oxidation dye precursors.

The second component (K2) of the first, second and fourth objects of the present disclosure is an oxidant preparation containing hydrogen peroxide in aqueous solution. The concentration of hydrogen peroxide in the oxidant preparation (K2) is determined on the one hand by the legal requirements and on the other hand by the desired effect; preferably from about 6 to about 12 wt. % solutions in water are used. Preparations (K2) preferred as contemplated herein are exemplified in that they contain about 1 to about 24% by weight, preferably from about 3 to about 12.5% by weight, particularly preferably from about 6 to about 10% by weight and especially from about 3 to about 6% by weight of hydrogen peroxide, in each case based on the weight of the oxidizing agent preparation (K2).

The mixing ratios of (K1) to (K2) by weight are to be selected accordingly so that the ready-to-use colorant contains, based on its weight, from about 0.5 to about 12% by weight, preferably from about 0.9 to about 7% by weight, particularly preferably from about 1.5 to about 5% by weight, exceptionally preferably from about 3 to about 4.5% by weight hydrogen peroxide (calculated as 100% $H_2O_2$).

Regarding further preferred embodiments of the multi-component packaging unit (kit-of-parts) as contemplated herein, what has been said about the techniques as contemplated herein applies mutatis mutandis.

For further fine nuancing of the desired red shade, the agents as contemplated herein may additionally contain one or more further oxidation dyes of the developer type. If in addition to the at least one oxidation dye precursor (A) at least one compound selected from the group including p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and/or the physiologically tolerated salts of these compounds is present, good results could be obtained. Particularly preferred from this group is the developer component 4-amino-3-methylphenol, also known as "oxyred".

In another particularly preferred embodiment, an agent as contemplated herein is exemplified in that it additionally contains one or more compounds from the group including p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and/or the physiologically tolerated salts of these compounds, preferably in a total amount of about 0.001 to about 0.4 wt. %, particularly preferably from about 0.01 to about 0.2 wt. %, extremely preferably from about 0.05 to about 0.1 wt. %, in each case based on the colorant ready for use as contemplated herein.

In a further particularly preferred embodiment, an agent as contemplated herein is exemplified in that it additionally contains 4-amino-3-methylphenol and/or a physiologically tolerated salt of this compound, preferably in a total amount of about 0.001 to about 0.4% by weight, particularly preferably from about 0.01 to about 0.2% by weight, exceptionally preferably from about 0.05 to about 0.1% by weight, in each case based on the ready-to-use colorant as contemplated herein.

In another particularly preferred embodiment, a kit as contemplated herein is exemplified in that the ODP-containing component (K1) additionally comprises one or more compounds selected from the group including p-aminophenol, 4-amino-3-methylphenol, 4-amino-2-aminomethylphenol, 4-amino-2-(1,2-dihydroxyethyl)phenol, 4-amino-2-(diethylaminomethyl)phenol, and/or the physiologically tolerated salts of these compounds, preferably in a total amount of about 0.002 to about 0.8 wt. %, particularly preferably from about 0.02 to about 0.4% by weight, exceptionally preferably from about 0.1 to about 0.2% by weight, in each case based on the weight of component (K1).

In a further particularly preferred embodiment, a kit as contemplated herein is exemplified in that the ODP-containing component (K1) additionally contains 4-amino-3-methylphenol and/or a physiologically tolerated salt of this compound, preferably in a total amount of about 0.002 to about 0.8% by weight, particularly preferably from about 0.02 to about 0.4% by weight, exceptionally preferably from about 0.1 to about 0.2% by weight, in each case based on the weight of component (K1).

Particularly preferred is furthermore an agent for the oxidative dyeing of keratinous fibers, containing in a cosmetic carrier—based on the total weight of the ready-to-use agent—(A) 4,5-diamino-1-(2-hydroxyethyl)-1H-pyrazole (structure I-A), present in a total amount of from about 0.01 to about 2.5% by weight, preferably from about 0.1 to about 1.8% by weight, particularly preferably from about 0.2 to about 1.0% by weight, exceptionally preferably from about 0.4 to about 0.9% by weight, the amounts being based on the weight of the free 4,5-diaminopyrazole base relative to the weight of the agent as contemplated herein, furthermore (B) glucoheptonic acid and/or at least one of its physiologically tolerated salts and/or lactones is/are present in a total amount of about 0.01 to about 2.5% by weight, preferably from about 0.05 to about 1.5% by weight, particularly preferably from about 0.1 to about 1.0% by weight, exceptionally preferably from about 0.1 to about 0.5% by weight, the amounts being based on the weight of free glucoheptonic acid in relation to the weight of the composition as contemplated herein, furthermore (C) at least one oxidizing agent other than atmospheric oxygen, and additionally, one or more compounds from the group including p-aminophenol, 4-amino-3-methylphenol, 4-amino-2-aminomethylphenol, 4-amino-2-(1,2-dihydroxyethyl) phenol, 4-amino-2-(diethylaminomethyl) phenol, and/or the physiologically tolerable salts of these compounds, in a total amount of about 0.001 to about 0.4% by weight, particularly preferably from about 0.01 to about 0.2% by weight, extremely preferably from about 0.05 up to about 0.1% by weight, based in each case on the ready-to-use colorant as contemplated herein.

Particularly preferred is an agent for the oxidative dyeing of keratinous fibers, containing in a cosmetic carrier—based on the total weight of the agent ready for use—.

(A) 4,5-diamino-1-(2-hydroxyethyl)-1H-pyrazole (structure I-A), present in a total amount of from about 0.01 to about 2.5% by weight, preferably from about 0.1 to about 1.8% by weight, particularly preferably from about 0.2 to about 1.0% by weight, exceptionally preferably from about 0.4 to about 0.9% by weight, the amounts being based on the weight of the free 4,5-diaminopyrazole base relative to the weight of the composition as contemplated herein, furthermore (B) Sodium glucoheptonate is/are present in a total amount of about 0.01 to about 2.5% by weight, preferably from about 0.05 to about 1.5% by weight, particularly preferably from about 0.1 to about 1.0% by weight, exceptionally preferably from about 0.1 to about 0.5% by weight, the amounts being based on the weight of free glucoheptonic acid relative to the weight of the composition as contemplated herein, furthermore (C) at least one oxidizing agent other than atmospheric oxygen, and additionally, one or more compounds from the group including p-aminophenol, 4-amino-3-methylphenol, 4-amino-2-aminomethylphenol, 4-amino-2-(1,2-dihydroxyethyl) phenol, 4-amino-2-(diethylaminomethyl) phenol, and/or the physiologically tolerable salts of these compounds, in a total amount of about 0.001 to about 0.4% by weight, particularly preferably from about 0.01 to about 0.2% by weight, extremely preferably from about 0.05 up to about 0.1% by weight, based in each case on the ready-to-use colorant as contemplated herein.

Particularly preferred is furthermore an agent for the oxidative dyeing of keratinous fibers, containing in a cosmetic carrier—based on the total weight of the ready-to-use agent—(A) 4,5-diamino-1-(2-hydroxyethyl)-1H-pyrazole (structure I-A), present in a total amount of from about 0.01 to about 2.5% by weight, preferably from about 0.1 to about 1.8% by weight, particularly preferably from about 0.2 to about 1.0% by weight, exceptionally preferably from about 0.4 to about 0.9% by weight, the amounts being based on the weight of the free 4,5-diaminopyrazole base relative to the weight of the composition as contemplated herein, furthermore (B) Sodium glucoheptonate is/are present in a total amount of about 0.01 to about 2.5% by weight, preferably from about 0.05 to about 1.5% by weight, particularly preferably from about 0.1 to about 1.0% by weight, exceptionally preferably from about 0.1 to about 0.5% by weight, the amounts being based on the weight of free glucoheptonic acid relative to the weight of the composition as contemplated herein, furthermore (C) at least one oxidizing agent other than atmospheric oxygen, and additionally, 4-amino-3-methylphenol and/or the physiologically tolerated salts of this compound, in a total amount of about 0.001 to about 0.4% by weight, particularly preferably from about 0.01 to about 0.2% by weight, exceptionally preferably from about 0.05 to about 0.1% by weight, in each case based on the ready-to-use colorant as contemplated herein.

Further colorants preferred as contemplated herein are exemplified in that additional oxidation dye precursors of the developer type are selected from the group formed by p-phenylenediamine, toluene-2,5-diamine, 2-(2,5-diaminophenyl)ethanol, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N, N'-bis-(4-aminophenyl)-1,3-diamino-propan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazol-1-one and their physiologically tolerated salts, or only in a total amount not exceeding about 0.08 wt. %, preferably not more than about 0.02% by weight, in each case based on the weight of the ready-to-use colorant as contemplated herein.

Preferred physiologically acceptable salts of the oxidation dye precursors having one or more amine groups are the hydrochlorides (monohydrochloride×HCl, or dihydrochloride×2 HCl), the sulfate (×H$_2$SO$_4$), and the hydrobromides (monohydrobromide×HBr, or dihydrobromide×2 HBr) of the compound.

Furthermore, the compositions as contemplated herein may also additionally contain one or more oxidation dye precursors of the coupler type. Coupler components alone do not form a significant coloration during oxidative dyeing, but always require the presence of developer components. Coupler components as contemplated herein allow at least one chemical substitution of a chemical residue of the coupler by the oxidized form of the developer component. In the process, covalent bonds are formed between the coupler and developer components.

As a coupler component suitable as contemplated herein, at least one compound is preferably selected from one of the following classes:

m-Aminophenol and/or derivatives thereof,
m-dihydroxybenzene and/or derivatives thereof,
m-diaminobenzene and/or derivatives thereof,
o-Diaminobenzene and/or derivatives thereof,
o-aminophenol derivatives, such as o-aminophenol,
Naphthalene derivatives having at least one hydroxy group,
Di- or trihydroxybenzene, respectively, and/or derivatives thereof,
Pyridine derivatives,
Pyrimidine derivatives,
Monohydroxyindole derivatives and/or monoaminoindole derivatives,
Monohydroxyindoline derivatives and/or monoaminoindoline derivatives,
Pyrazolone derivatives, such as 1-phenyl-3-methylpyrazol-5-one,
Morpholine derivatives, such as 6-hydroxybenzomorpholine or 6-aminobenzomorpholine,
Quinoxaline derivatives, such as 6-methyl-1,2,3,4-tetrahydroquinoxaline.

Mixtures of two or more compounds from one or more of these classes are also contemplated in the context of this embodiment.

Another preferred embodiment is an agent as contemplated herein and exemplified in that it additionally comprises at least one coupler-type oxidation dye precursor selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and/or 7-hydroxyindoline and their physiologically tolerated salts.

In principle, the compositions as contemplated herein can also contain at least one direct dye selected from the group including anionic, nonionic and/or cationic dyes.

Particularly preferred are one or more nonionic direct dyes from the group, HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

In another particularly preferred embodiment, the agent as contemplated herein is exemplified in that it additionally contains one or more nonionic direct dyes from the group including HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

In addition, anionic direct dyes known by the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue may also be present.

Suitable cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B) and direct dyes containing a heterocycle containing at least one quaternary nitrogen atom, in particular Basic Yellow 87, Basic Orange 31 and Basic Red 51. The cationic direct dyes marketed under the trademark Arianor are also suitable cationic direct dyes as contemplated herein.

The additional oxidation dye precursors, i.e., developer components which are different from the compounds of group (A), further coupler components as well as the optionally additionally contained direct dyes may be present, for example, in an amount of about 0.0001 to about 5.0% by weight, preferably from about 0.001 to about 0.5% by weight, in each case based on the total weight of the composition as contemplated herein.

Furthermore, the compositions as contemplated herein may contain additional active ingredients, auxiliaries and additives, such as nonionic polymers like vinylpyrrolidinone/vinyl acrylate copolymers, polyvinylpyrrolidinone, vinylpyrrolidinone/vinyl acetate copolymers, polyethylene glycols and polysiloxanes; additional silicones such as volatile or non-volatile, straight-chain, branched or cyclic, cross-linked or non-crosslinked polyalkylsiloxanes (such as dimethicone or cyclomethicone), polyarylsiloxanes and/or polyalkylarylsiloxanes, in particular polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes with quaternary groups, dimethyldiallyl ammonium chloride polymers, acrylamide-dimethyldiallyl ammonium chloride copolymers, diethyl sulfate quaternized dimethylamino-ethyl methacrylate-vinylpyrrolidinone copolymers, vinylpyrrolidinone-imidazolinium methochloride copolymers and quaternized polyvinyl alcohol; zwitterionic and amphoteric polymers; anionic polymers such as polyacrylic acids or crosslinked polyacrylic acids; structurants such as glucose, maleic acid and lactic acid, hair conditioning compounds such as phospholipids, for example lecitin and cephalins; perfume oils, dimethyl isosorbide and cyclodextrins; fiber structure-improving agents, in particular mono-, di- and oligosaccharides such as glucose, galactose, fructose, fructose and lactose; dyes for coloring the product; antidandruff agents such as piroctone olamine, zinc omadine and climbazole; amino acids and oligopeptides; Protein hydrolysates on animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinone carboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and kerosene's; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; pigments as well as blowing agents such as propane-butane mixtures, $N_2O$, dimethyl ether, $CO_2$ and air.

A further object of the present disclosure is a process for the oxidative hair dyeing of keratinous fibers, in particular human hair, in which an agent as contemplated herein or preferred as contemplated herein, in particular an agent according to one of claims 1 to 7, is applied to the fibers, in particular the hair, is left there for a time of from about 1 to about 60 minutes, preferably from about 20 to about 45 minutes, where it is left on the fibers, in particular the hair, at room temperature and/or at least about 30° C., the fibers, in particular the hair, are then rinsed with water and/or a cleansing composition and, if desired, an aftertreatment agent is applied to the fibers, in particular the hair, which is optionally rinsed out, and the fibers, in particular the hair, are then dried.

A further object of the present disclosure is a process for the oxidative hair dyeing of keratinous fibers, in particular human hair, in which the components of a kit as contemplated herein or preferred as contemplated herein, in particular a kit according to one of claims 8 to 11, are applied to the fibers, in particular the hair, simultaneously or directly one after the other without rinsing, are left there for a time of from about 1 to about 60 minutes, preferably from about 20 to about 45 minutes, at room temperature and/or at least about 30° C., the fibers, in particular the hair, are then rinsed with water and/or a cleansing composition and, if desired, an aftertreatment agent is applied to the fibers, in particular the hair, which is optionally rinsed out, and the fibers, in particular the hair, are then dried.

As contemplated herein, the term "Room temperature" denotes the temperature in the room in which a person usually uses a hair dye, usually a bathroom or a hairdressing salon, where a temperature in the range from about 10-29° C. prevails.

Leaving the hair coloring application mixture on the fibers, in particular the hair, can also be done at least at about 30° C., preferably at about 30-60° C., particularly preferably at about 32-50° C., if the hair is heated, for example, with a heat hood or with a radiant heater.

The oxidizing agent preparation (K2) used in dyeing kits as contemplated herein and in dyeing processes preferred as contemplated herein contains, in each case based on its weight, preferably from about 40-about 96% by weight, particularly preferably from about 70-about 93% by weight, exceptionally preferably from about 80-about 90% by weight, of water.

The oxidizing agent preparation (K2) used in dyeing kits as contemplated herein and in dyeing processes preferred as contemplated herein further contains, in each case based on its weight, preferably about 0.5 to about 23% by weight, further preferably from about 2.5 to about 21% by weight, particularly preferably from about 4 to about 20% by weight, most preferably from about 5 to about 18% by weight and exceptionally preferably from about 6 to about 12% by weight, of hydrogen peroxide.

To stabilize the hydrogen peroxide, the oxidant preparation (K2) preferably has a pH in the range from about 2.0 to about 6.5, particularly preferably from about 2.5-about 5.5, exceptionally preferably from about 2.8 to about 5.0, in each case measured at 20° C.

Cationic Surfactant in the Oxidant Preparation (K2)

The oxidant preparation (K2) usually has a viscosity in the range of about 10-6000 mPas, preferably about 200-5000 mPas, particularly preferably about 1000-4500 mPas, measured at 20° C. in each case. For application to the hair, however, the application mixture should have a significantly higher viscosity so that it remains on the hair for the entire application time (in the range of about 5-about 60 minutes, preferably from about 30-about 45 minutes) and does not drip down. A distinction is made between whether the application mixture is prepared by shaking both compositions (K1) and (K2) in an application bottle, from which the application mixture is applied to the hair immediately after mixing with the aid of an application spout as a bottle top (bottle application), or whether the application mixture is prepared by mixing both compositions (K1) and (K2) in a bowl, from which the application mixture is applied to the hair with a brush immediately after mixing (brush application). The bottle application is particularly suitable for colorants that are sold in retail outlets with a recommendation for use by the consumer himself. Brush application is particularly suitable for colorants that are prepared in the hairdressing salon by the hairdresser and applied to the consumer's hair.

Surprisingly, it was found that an application mixture with a viscosity suitable for brush application is obtained when a component (K1) as contemplated herein or preferred as contemplated herein is mixed with an oxidant preparation (K2) containing at least one cationic surfactant, when (K1) contains an anionic surfactant. Upon mixing, the interaction between anionic components in (K1) and the at least one cationic surfactant leads to the desired increase in viscosity. The resulting paste-like consistency of the application mixture leads to optimal application properties, especially for brush application. The application mixtures obtained in this way, in particular the mixtures whose mixing ratio (K1):(K2) by weight is in the range from about 1:0.8 to about 1:2.5, particularly preferably in the range from about 1:1 to about 1:2, preferably have a viscosity in the range from about 20000-about 100000 mPas, preferably from about 30000-about 80000 mPas, particularly preferably from about 45000-about 70000 mPas, in each case measured at 20° C. (Brookfield viscometer, rotational frequency of 4 min−1, spindle No. 5).

In a further preferred embodiment of the present disclosure, the oxidant preparation (K2) used as contemplated herein contains at least one cationic surfactant, preferably in a total amount of about 0.05-about 3% by weight, particularly preferably of about 0.1-about 1.5% by weight, extremely preferably of about 0.3-about 0.9% by weight, in each case based on the weight of the oxidant preparation (K2).

Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Cationic surfactants adsorb at interfaces and aggregate in aqueous solution above the critical micelle formation concentration to form positively charged micelles.

As contemplated herein, cationic surfactants of the type of quaternary ammonium compounds, esterquats and alkylamidoamines are preferred. Preferred quaternary ammonium compounds are ammonium halides, such as alkyltrimethylammonium chlorides, dialkyldimethylammonium chlorides, trialkylmethylammonium chlorides, as well as the imidazolium compounds known under the INCI designations Quaternium-27 and Quaternium-83. Other preferred quaternary ammonium compounds are tetraalkylammonium salts, such as in particular the quaternium-52 known under the INCI designation, a poly(oxy-1,2-ethanediyl), ((octadecylnitrilio)tri-2,1-ethanediyl)tris(hydroxy)phosphate (1:1) salt, which has the general structural formula (III), wherein x+y+z=10:

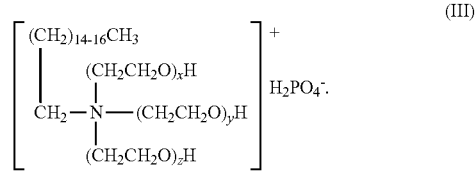

The long alkyl chains of the surfactants mentioned above preferably have 10 to 22, particularly preferably 12 to 18 carbon atoms. Behenyl trimethylammonium chloride, stearyl trimethylammonium chloride and cetyl trimethylammonium chloride are particularly preferred, with stearyl trimethylammonium chloride being extremely preferred. Further cationic surfactants suitable as contemplated herein are quaternized protein hydrolysates. Alkylamidoamines are usually produced by amidation of natural or synthetic fatty acids and fatty acid cuts with dialkylaminoamines Tegoamid® S 18 (stearamidopropyldimethylamine) is a suitable compound from this group of substances. Esterquats are substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyl dialkylamines. Such products are sold under the Stepantex®, Dehyquart® and Armocare® trademarks.

In terms of optimum application properties and optimal dyeing results, C10-C22 alkyltrimethylammonium chlorides have proven to be particularly suitable. Particularly preferred oxidizing agent preparations (K2) used as contemplated herein are therefore exemplified in that they are extremely preferred with at least one cationic surfactant in a total amount of about 0.05-about 3% by weight, particularly preferably from about 0.1-about 1.5% by weight, very particularly preferably from about 0.3 to about 0.9% by weight, based in each case on the weight of the oxidizing agent preparation (K2). The cationic surfactant is preferably at least one surfactant selected from C10-C22-alkyltrimethylammonium chlorides, in particular selected from behenyltrimethylammonium chloride, stearyltrimethylammonium chloride and cetyltrimethylammonium chloride, and mixtures of these surfactants. Extremely preferred oxidant preparations (K2) used as contemplated herein contain stearyl trimethylammonium chloride in a total amount of about 0.05-about 3 wt. %, particularly preferably from about 0.1-about 1.5 wt. %, extremely preferably from about 0.3-about 0.9 wt. %, each based on the weight of the oxidant preparation (K2).

A further packaging unit (kit-of-parts) preferred as contemplated herein is exemplified in that the oxidizing agent preparation (K2) contains at least one cationic surfactant, preferably in a total amount of about 0.05-about 3 wt. %, particularly preferably from about 0.1-about 1.5 wt. %, extremely preferably from about 0.3-about 0.9% by weight, in each case based on the weight of the oxidant preparation (K2), but no polymer with a degree of polymerization of at least about 200 and no polymer with a molecular weight of about 10,000 daltons or higher.

A further packaging unit (kit-of-parts) preferred as contemplated herein is exemplified in that the oxidizing agent preparation (K2) contains at least one cationic surfactant, preferably selected from stearyl trimethylammonium chloride, in a total amount of about 0.05-about 3 wt.-%, particularly preferably from about 0.1-about 1.5% by weight, extremely preferably from about 0.3-about 0.9% by weight, in each case based on the weight of the oxidant preparation (K2), but does not contain any polymer with a degree of polymerization of at least about 200 and no polymer with a molecular weight of about 10,000 daltons or higher.

A preferred process for oxidative hair dyeing as contemplated herein is exemplified in that the oxidant preparation (K2) contains at least one cationic surfactant, preferably in a total amount of about 0.05-about 3 wt. %, particularly preferably of about 0.1-about 1.5 wt. %, extremely preferably of about 0.3-about 0.9% by weight, in each case based on the weight of the oxidant preparation (K2), but does not contain a polymer having a degree of polymerization of at least about 200 and a polymer having a molecular weight of about 10,000 Daltons or higher.

A further method for oxidative hair dyeing preferred as contemplated herein is exemplified in that the oxidant preparation (K2) contains at least one cationic surfactant, preferably selected from stearyl trimethyl ammonium chloride, in a total amount of about 0.05-about 3 wt. %, particularly preferably from about 0.1-about 1.5 wt. %, exceptionally preferably from about 0.3-about 0.9 wt. %, each based on the weight of the oxidant preparation (K2), but does not contain a polymer having a degree of polymerization of at least about 200 and a polymer having a molecular weight of about 10,000 Daltons or higher.

Surprisingly, it was found that an application mixture with a viscosity suitable in particular for bottle application is obtained when a component (K1) as contemplated herein or preferred as contemplated herein is mixed with an oxidant preparation (K2) containing at least one copolymer selected from crosslinked acrylic acid/acrylic acid C1-C6 alkyl ester copolymers and crosslinked methacrylic acid/acrylic acid C1-C6 alkyl ester copolymers, preferably in a total amount of about 0.1-about 7 wt. %, particularly preferably from about 0.5-about 6% by weight, exceptionally preferably 1-4.5% by weight, in each case based on the weight of the oxidizer preparation (K2). Mixing the agent as contemplated herein or the preferred agent as contemplated herein with such an oxidizing agent preparation (K2) leads to the desired increase in viscosity. The resulting medium viscous consistency of the application mixture leads to optimal application properties, especially for bottle application. The application mixtures obtained in this way, at weight-related mixing ratios (K1):(K2) in the range from about 1:0.8 to about 1:2.5, particularly preferably in the range from about 1:1 to about 1:2, preferably have a viscosity in the range from about 10000-about 50000 mPas, preferably from about 15000-about 30000 mPas, particularly preferably from about 18000-about 25000 mPas, in each case measured at 20° C. (Brookfield viscometer, rotational frequency 4 min−1, spindle No. 5).

A further packaging unit (kit-of-parts) preferred as contemplated herein is therefore exemplified in that the oxidizing agent preparation (K2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of about 0.1-about 7 wt. %, particularly preferably from about 0.5-about 6% by weight, extremely preferably from about 1-about 4.5% by weight, in each case based on the weight of the oxidizing agent preparation (K2), and preferably contains no cationic surfactant.

A further process for oxidative hair dyeing preferred as contemplated herein is therefore exemplified in that the oxidant preparation (K2) contains at least one copolymer selected from crosslinked acrylic acid/acrylic acid C1-C6 alkyl ester copolymers and crosslinked methacrylic acid/acrylic acid C1-C6 alkyl ester copolymers, preferably in a total amount of about 0.1-about 7 wt. %, particularly preferably from about 0.5-about 6 wt. %, exceptionally preferably from about 1-about 4.5% by weight, in each case based on the weight of the oxidizer preparation (K2), and preferably contains no cationic surfactant.

Preferred crosslinked copolymers of this type are selected from—respectively crosslinked—methacrylic acid/methyl acrylate, methacrylic acid/ethyl acrylate, methacrylic acid/propyl acrylate, methacrylic acid/butyl acrylate, methacrylic acid/pentylacrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentylacrylate and acrylic acid/hexyl acrylate copolymers and mixtures thereof.

A further packaging unit (kit-of-parts) preferred as contemplated herein is exemplified in that the oxidizing agent preparation (K2) contains at least one cross-linked copolymer selected from—in each case cross-linked—methacrylic acid/methyl acrylate, methacrylic acid/ethyl acrylate, methacrylic acid/propyl acrylate, methacrylic acid/butyl acrylate, methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof, in a total amount of about 0.1-about 7 wt.-%, particularly preferably from about 0.5-about 6 wt. %, extremely preferably from about 1-about 4.5 wt. %, each based on the weight of the oxidant preparation (K2), and contains no cationic surfactant.

A further process for oxidative hair dyeing preferred as contemplated herein is exemplified in that the oxidant preparation (K2) comprises at least one crosslinked copolymer selected from—in each case crosslinked—methacrylic acid/methyl acrylate, methacrylic acid/ethyl acrylate, methacrylic acid/propyl acrylate, methacrylic acid/butyl acrylate, methacrylic acid/pentylacrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentylacrylate and acrylic acid/hexyl acrylate copolymers and mixtures thereof, in a total amount of about 0.1-about 7 wt. %, particularly preferably from about 0.5-about 6 wt. %, exceptionally preferably from about 1-about 4.5 wt. %, in each case based on the weight of the oxidant preparation (K2), and contains no cationic surfactant.

The oxidizing agent preparations (K2) used as contemplated herein and preferably used as contemplated herein may also contain stabilizers, especially complexing agents, and pH buffer substances.

In a further preferred embodiment of the present disclosure, the oxidizing agent preparation (K2) used as contemplated herein contains at least one oil in a total amount of about 0.2-about 50% by weight, preferably from about 2-about 40% by weight, particularly preferably from about 8-about 30% by weight, extremely preferably from about 15-about 25% by weight, in each case based on the weight of the oxidizing agent preparation (K2).

In a particularly preferred embodiment of the present disclosure, the oxidizing agent preparation (K2) used as contemplated herein contains no cationic surfactant and at least one oil in a total amount of about 0.2-about 50% by weight, particularly preferably from about 2-about 40% by weight, extremely preferably from about 8-about 30% by weight, further extremely preferably from about 15-about 25% by weight, in each case based on the weight of the oxidizing agent preparation (K2).

The at least one oil present in the oxidizer preparation (K2) in a total amount of about 0.2-about 50 wt. %, based on the weight of the preparation (K2), is preferably selected from natural and synthetic hydrocarbons, particularly preferably from mineral oil, paraffin oils, $C_{18}$-$C_{30}$ isoparaffins, in particular isoeicosane, polyisobutenes and polydecenes, $C_8$-$C_{16}$ isoparaffins, and 1,3-di(2-ethylhexyl)cyclohexane; the benzoic acid esters of linear or branched $C_{8-22}$ alkanols; triglycerides of linear or branched, saturated or unsaturated, optionally hydroxylated $C_{8-30}$ fatty acids, especially natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$ alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear, branched or cyclic $C_2$-$C_{18}$ alkanols or with polyvalent linear or branched $C_2$-$C_6$ alkanols; silicone oils and mixtures of the aforementioned substances. Oils particularly preferred in this connection as contemplated herein are selected from paraffin oils and the esters of linear or branched saturated or unsaturated fatty alcohols having 2-30 carbon atoms with linear or branched saturated or unsaturated fatty acids having 2-30 carbon atoms, which may be hydroxylated, and mixtures thereof; extremely preferably selected from paraffin oil, isopropyl palmitate and isopropyl myristate and mixtures thereof.

In a further preferred embodiment of the present disclosure, the oxidizing agent preparation (K2) used as contemplated herein contains at least one surfactant selected from anionic surfactants and non-ionic surfactants and mixtures thereof in a total amount of about 0.05-about 2 wt. %, preferably from about 0.3-about 1.5 wt. %, of the oxidizing agent preparation (K2), and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of about 1-about 5% by weight, preferably from about 1.5-about 4% by weight, all the quantitative data being based on the weight of the oxidizing agent preparation (K2), and the preparation (M2) containing no cationic surfactants, no oils, no polymer with a degree of polymerization of at least about 200 and no polymer with a molecular weight of about 10,000 daltons or higher.

A further kit-of-parts preferred as contemplated herein and a further hair dyeing process preferred as contemplated herein are each exemplified in that the oxidant preparation (K2) comprises at least one surfactant selected from anionic surfactants and non-ionic surfactants and mixtures thereof in a total amount of about 0.05-about 2% by weight, preferably from about 0.3-about 1.5% by weight, and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of about 1-about 5% by weight, preferably from about 1.5-about 4% by weight, in each case based on the weight of the oxidant preparation (K2).

A further kit-of-parts preferred as contemplated herein and a further hair dyeing process preferred as contemplated herein are each exemplified in that the oxidant preparation (K2) comprises at least one surfactant selected from anionic surfactants and non-ionic surfactants and mixtures thereof in a total amount of about 0.05-about 2% by weight, preferably from about 0.3-about 1.5% by weight, and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol), and mixtures thereof, in a total amount of about 1-about 5 wt. %, preferably from about 1.5-about 2 wt. %, preferably from about 0.3-about 1.5 wt. %, preferably from about 1.5-about 4% by weight, each based on the weight of the oxidant preparation (K2), but does not contain a polymer having a degree of polymerization of at least about 200 and a polymer having a molecular weight of about 10,000 daltons or higher.

It was found that the thickening by employing the interaction between the copolymer in the agent of the present disclosure and the surfactant/1-alkanol mixture in the oxidizer preparation (K2) is sufficient and cannot be further increased or even impaired in its application properties by the presence of a polymer with a degree of polymerization of at least about 200 or a polymer with a molecular weight of about 10,000 daltons or higher.

A further kit-of-parts preferred as contemplated herein and a further hair dyeing process preferred as contemplated herein are each exemplified in that the oxidant preparation (K2) comprises at least one surfactant selected from anionic surfactants and non-ionic surfactants and mixtures thereof in a total amount of about 0.05-about 2% by weight, preferably from about 0.3-about 1.5% by weight, at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) as well as mixtures thereof, in a total amount of about 1-about 5 wt. %, preferably from about 1.5-about 4 wt. %, and at least one oil in a total amount of about 0.2 from about 50% by weight, preferably from about 2-about 40% by weight, particularly preferably from about 8-about 30% by weight, exceptionally preferably from about 15-about 25% by weight, in each case based on the weight of the oxidant preparation (K2).

A further kit-of-parts preferred as contemplated herein and a further hair dyeing process preferred as contemplated herein are each exemplified in that the oxidant preparation (K2) comprises at least one surfactant selected from anionic surfactants and non-ionic surfactants and mixtures thereof in a total amount of about 0.05-about 2 wt. %, preferably from about 0.3-about 1.5 wt. %, at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol), and mixtures thereof, in a total amount of about 1-about 5 wt. %, preferably from about 1.5-about 4 wt. %, and at least one oil in a total amount of about 0.2-about 50 wt. %, preferably from about 2-about 40 wt. %, particularly preferably from about 8-about 30 wt. %, exceptionally preferably from about 15-about 25 wt. %, in each case based on the weight of the oxidant preparation (K2), but does not contain a polymer having a degree of polymerization of at least about 200 and a polymer having a molecular weight of about 10,000 Daltons or higher.

Suitable anionic surfactants for the oxidant preparations (K2) used as contemplated herein are all anionic surfactants discussed above for the agents as contemplated herein.

Suitable nonionic surfactants for the oxidant preparations (K2) used as contemplated herein are all nonionic surface-active agents suitable for use on the human body, as discussed above for the agents as contemplated herein.

The following examples are intended to illustrate the subject matter of the present disclosure without limiting it herein.

1.1. Production of Dyes

The following color creams were produced (all figures are in percent by weight unless otherwise stated):

|  | Cream No. 1 Component (K1) of the fourth subject matter of the present disclosure or Component (K1) comparison | Cream No. 2 Component (K1) of the second subject matter of the present disclosure |
|---|---|---|
| 1-Hydroxyethyl 4,5-diaminopyrazole sulfate | 1.50 | 1.50 |
| 4-amino-2-hydroxytoluene | 0.30 | 0.30 |
| 4-Amino-m-cresol | 0.18 | 0.18 |
| m-Aminophenol | 0.60 | 0.60 |
| Sodium glucoheptonate | — | 0.90 |
| Ammonium hydroxide | 3.20 | 3.20 |
| Monoethanolamine | 0.60 | 0.60 |
| Potassium hydroxide | 0.06 | 0.06 |
| Octyldodecanol | 1.60 | 1.60 |
| Cetearyl alcohol | 9.60 | 9.60 |
| Glyceryl stearate (self-emulsifying) | 3.00 | 3.00 |
| Ceteareth-20 | 2.40 | 2.40 |
| Sodium laureth sulfate | 0.90 | 0.90 |
| Sodium cetaryl sulphate | 0.50 | 0.50 |
| Oleic acid | 0.30 | 0.30 |
| Sodium sulphite | 0.40 | 0.40 |
| Perfume | 0.30 | 0.30 |
| Propylene glycol | 0.02 | 0.02 |
| Glycerine | 0.20 | 0.20 |
| Tetrasodium EDTA | 0.20 | 0.20 |
| Carbomer | 0.12 | 0.12 |
| Ascorbic acid | 0.05 | 0.05 |
| Sodium sulphate | 0.02 | 0.02 |
| Sodium benzoate | 0.01 | 0.01 |
| Water | 73.94 | 73.04 |

Oxidizer Component (K2)

| Hydrogen peroxide | 6.0 |
|---|---|
| Cetearyl alcohol | 1.6 |
| PEG-40 Castor Oil | 0.3 |
| Disodium pyrophosphate | 0.3 |
| Sodium cetaryl sulphate | 0.2 |
| Disodium EDTA | 0.1 |
| Sodium benzoate | 0.04 |
| Phosphoric acid | 0.03 |
| Water | 91.43 |

Component (K3) of the Fourth Article of the Present Disclosure

| Sodium glucoheptonate | 8.00 |
|---|---|
| Polyvinylpyrrolidone with K-value 27-33 | 10.00 Active substance |
| Phenoxyethanol | 0.60 |
| Ethylhexylglycerol | 0.09 |
| Keratin hydrolysate | 0.01 |
| Water | 81.30 |

The comparative colorant (V1) was prepared by mixing Cream No. 1 and the oxidant component (K2) in equal parts by weight (1:1).

A coloring agent (E1) according to the first subject matter of the present disclosure was prepared by mixing cream No. 2 (as component (K1) of the second subject matter of the present disclosure) and the oxidizing agent component (K2) in equal parts by weight (1:1), respectively.

A coloring agent (E4) according to the first subject matter of the present disclosure was obtained by mixing cream No. 1 (as component (K1) of the fourth subject matter of the present disclosure) with the oxidizing agent component (K2) and the above-mentioned component (K3) in the weight ratio (K1):(K2):(K3) of 60:60:1.8 produced.

1.2 Staining on the Keratin Fibers

Normal bleached hair strands of the brand Kerling 7-0, 1×ultra-bleached, about 1 gram) were treated as follows.

One of each of the colorants (V1), (E1) or (E4) was applied to the hair strands immediately after its preparation (liquor ratio 4 grams of ready-to-use colorant (V1), (E1) or (E4) per gram of hair) and left on the hair for an exposure time of 30 Minutes at room temperature (22° C.). The dye was then rinsed out of the strands with water. The strands were first dried with a towel and then in a stream of cold air. All the strands were intensely dyed red.

1.3 Measurement of Wash Fastness

For the evaluation of the wash fastness or wash resistance of the dyeing, a 2 wt. % aqueous solution of the shampoo tabulated below was added to an ultrasonic bath.

| | |
|---|---|
| Sodium laureth sulfate | 8.50 |
| Disodium cocoamphodiacetate | 0.80 |
| Cocamidopropyl betaine | 1.70 |
| Laureth-4 | 0.30 |
| PEG-40 Hydrogenated Castor Oil | 0.10 |
| PEG-7 Glyceryl cocoate | 0.60 |
| Cocamide MEA | 0.50 |
| Hydrogenated Castor Oil | 0.10 |
| Sodium hydroxide | 0.05 |
| Citric acid | 0.40 |
| Sodium chloride | 1.60 |
| Sodium benzoate | 0.50 |
| Glycol distearate | 0.60 |
| Jojoba oil | 0.01 |
| Polyquaternium-10 | 0.10 |
| Perfume | 0.30 |
| Water | 83.84 |

The hair strands were immersed in this solution up to the ends and treated with ultrasound (11 minutes in the ultrasound bath correspond to 6 hand washes; the washing solution was changed after each wash). Then the strands were rinsed with lukewarm tap water for one minute and dried in a stream of cold air.

All hair strands were colorimetrically measured at four different measuring points along the strand before dying, after dyeing and after simulated 24 washes, i.e., after four 11-minute ultrasonic baths.

To determine the wash resistance, color measurements were carried out according to the L*a*b* color system.

Three hair strands were used for each of the 3 colorants (V1), (E1) or (E4) and the arithmetic mean of each wash cycle was calculated for all hair strands. From the measured L*a*b* values, the color difference ΔE between the color of the dyed, unshampooed hair (value combination $L_0^*$, $a_0^*$, $b_0^*$) and the color of the dyed, shampooed hair after simulated 24 washes (value combination $L_i^*$, $a_i^*$, $b_i^*$) was calculated according to the following formula:

$$\Delta E = ((L_i - L_0)^2 + (a_i - a_0)^2 + (b_i - b_0)^2)^{1/2}$$

The greater the ΔE value, the more pronounced the color difference and the lower the wash fastness or wash resistance of the dyeing. Color differences with ΔE<1 are not perceptible to the human eye. Color differences with ΔE<2 are only visible to the trained eye. Color differences with ΔE>2 are visible even to the untrained eye.

Results of Color Measurements for Fastness to Washing

| Colorants | ΔE | ΔΔE to (V1) |
|---|---|---|
| (V1) | 11.3 | |
| (E1) | 8.8 | 2.5 |
| (E4) | 8.3 | 3.0 |

The colorants (E1) and (E4) as contemplated herein, each containing sodium glucoheptonate, show a markedly lower color difference, i.e., a markedly improved fastness to washing or wash resistance of the dyeing, compared with the colorant (V1) not contemplated herein without glucoheptonic acid and/or at least one of its physiologically tolerated salts and/or lactones after simulated 24 washing cycles, i.e., after four times 11 minutes of ultrasonic bathing in a shampoo solution.

1.4 Selectivity Measurement

To determine whether the initial color result was uniform along the hair fiber from root to tip, the half of the hair strand close to the root was bleached once, corresponding to moderate damage, and the other half of the hair strand close to the tip was bleached twice, corresponding to very severe damage, after two smoothing treatments.

To assess selectivity, the color distance ΔE* between the near-root strand half and the near-tip strand half was determined.

The greater the value for ΔE, the more pronounced the color difference between the two halves of the strand and the lower the homogeneity or uniformity of the coloration or the higher the selectivity of the coloration.

Results of Color Measurements for Selectivity

| Colorants | ΔE | ΔΔE to (V1) |
|---|---|---|
| (V1) | 2.2 | |
| (E1) | 0.9 | 1.3 |
| (E4) | 1.6 | 0.6 |

The colorants (E1) and (E4) as contemplated herein, each containing sodium glucoheptonate, show a lower color difference between strand sections with different degrees of damage, i.e., a significantly improved homogeneity or uniformity of the coloration and a reduced selectivity of the coloration, compared with the colorant (V1) not contemplated herein without glucoheptonic acid and/or at least one of its physiologically compatible salts and/or lactones.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for the oxidative dyeing of keratinous fibers, comprising in a cosmetic carrier
   (A) at least one oxidation dye precursor of structure (I) and/or one of its physiologically tolerable salts

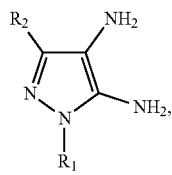

wherein $R_1$ and $R_2$ are independently hydrogen or a linear or branched C1-C10 alkyl group which may be substituted with one to ten hydroxyl groups, $R_1$ and $R_2$ not being hydrogen at the same time,
   (B) glucoheptonic acid and/or at least one of its physiologically tolerated salts and/or lactones, and
   (C) at least one oxidizing agent other than atmospheric oxygen.

2. The agent according to claim 1, wherein the agent comprises the at least one oxidation dye precursor of structure (I) in which $R_1$ is a linear or branched $C_1$-$C_{10}$ alkyl group which may be substituted by one to ten hydroxyl groups and $R_2$ is hydrogen.

3. The agent according to claim 1, wherein the agent comprises the at least one oxidation dye precursor of structure (I) in which $R_1$ represents a 2-hydroxyethyl group and $R_2$ represents hydrogen, such that the at least one oxidation dye precursor of structure (I) is 4,5-diamino-1-(2-hydroxyethyl)-1H-pyrazole and/or one of its physiologically tolerated salts.

4. The agent according to claim 1, wherein the agent comprises the at least one oxidation dye precursor of structure (I), in which $R_1$ represents an n-hexyl group and $R_2$ represents hydrogen.

5. The agent according to claim 1, wherein the agent comprises sodium glucoheptonate as the physiologically tolerated salt of glucoheptonic acid.

6. The agent according to claim 1, wherein the agent comprises—based on its total weight—the glucoheptonic acid or at least one of its physiologically tolerated salts and/or lactones in a total amount of from about 0.01 to about 2.5% by weight, the amount being based on the weight of free glucoheptonic acid in relation to the weight of the agent.

7. The agent according to claim 1, wherein the at least one oxidizing agent other than atmospheric oxygen is selected from hydrogen peroxide, percarbonates, persalts, and mixtures thereof.

8. A multicomponent kit-of-parts for oxidative dyeing of keratinous fibers, comprising at least two separately prepared components (K1) and (K2), wherein
   the first component (K1) in a cosmetic carrier comprises
   (A) at least one oxidation dye precursor of the structure (I) and/or one of its physiologically tolerated salts

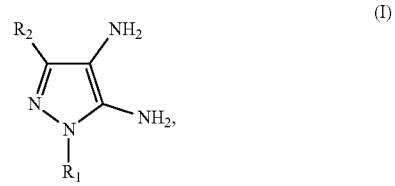

wherein $R_1$ and $R_2$ are independently hydrogen or a linear or branched C1 C10 alkyl group which may be substituted with one to ten hydroxyl groups, $R_1$ and $R_2$ not being hydrogen at the same time,
   the second component (K2)
   comprises water,
   wherein
   (B) the kit-of-parts comprises glucoheptonic acid and/or at least one of its physiologically tolerated salts and/or lactones, and
   the kit-of-parts comprises an oxidizing agent (C).

9. The multicomponent kit-of-parts for oxidative dyeing of keratinous fibers of claim 8, comprising the at least two separately prepared components (K1) and (K2), wherein
   the second component (K2) comprises the oxidizing agent, wherein the oxidizing agent comprises hydrogen peroxide.

10. The multicomponent kit-of-parts for oxidative dyeing of keratinous fibers of claim 8, further comprising a third separately prepared component (K3), wherein
    the second component (K2) comprises
    (C) the oxidizing agent, wherein the oxidizing agent comprises hydrogen peroxide, and wherein the hydrogen peroxide is dissolved in the water, and
    the third component (K3)
    (B) comprises the glucoheptonic acid and/or at least one of its physiologically tolerated salts and/or lactones.

11. The multicomponent kit-of-parts for oxidative dyeing of keratinous fibers of claim 8, further comprising a third prepared component (K3), wherein
    the first component (K1) in a cosmetic carrier comprises
    (C) sodium percarbonate as the oxidizing agent and optionally at least one further oxidizing agent selected from the persalts, peroxodisulfate salts and/or peroxomonosulfate salts,
    the third component (K3)
    (B) comprises the glucoheptonic acid and/or at least one of its physiologically tolerated salts and/or lactones.

12. A method for the oxidative dyeing of keratinous fibers, the method comprising the steps of:
applying an agent to the keratinous fibers, wherein the agent comprises:
(A) at least one oxidation dye precursor of structure (I) and/or one of its physiologically tolerable salts

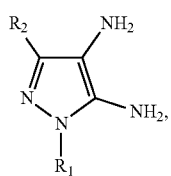
(I)

wherein $R_1$ and $R_2$ are independently hydrogen or a linear or branched C1-C10 alkyl group which may be substituted with one to ten hydroxyl groups, $R_1$ and $R_2$ not being hydrogen at the same time,
(B) glucoheptonic acid and/or at least one of its physiologically tolerated salts and/or lactones, and
(C) at least one oxidizing agent other than atmospheric oxygen;
leaving the agent on the fibers for a time of from about 1 to about 60 minutes;
rinsing the fibers, with water and/or a cleansing composition;
optionally applying an aftertreatment agent to the fibers; and optionally rinsing the aftertreatment agent out of the fibers.

13. The method of oxidative hair dyeing of claim 12, wherein
the (A) at least one oxidation dye precursor, (B) the glucoheptonic acid, and (C) the at least one oxidizing agent are components of the agent, and wherein
the components of the agent are applied simultaneously to the keratinous fibers.

14. The multicomponent kit-of-parts for oxidative dyeing of keratinous fibers of claim 8, wherein the $R_1$ of the at least one oxidation dye precursor of structure (I) is a linear or branched $C_1$-$C_{10}$ alkyl group which may be substituted by one to ten hydroxyl groups and $R_2$ is hydrogen.

15. The multicomponent kit-of-parts for oxidative dyeing of keratinous fibers of claim 8, wherein the $R_1$ of the at least one oxidation dye precursor of structure (I) represents a 2-hydroxyethyl group and $R_2$ represents hydrogen, such that the at least one oxidation dye precursor of structure (I) is 4,5-diamino-1-(2-hydroxyethyl)-1H-pyrazole and/or one of its physiologically tolerated salts.

16. The multicomponent kit-of-parts for oxidative dyeing of keratinous fibers of claim 8, wherein the $R_1$ of the at least one oxidation dye precursor of structure (I) represents an n-hexyl group and $R_2$ represents hydrogen.

17. The agent of claim 1, wherein the at least one oxidative dye precursor is present in the agent in an amount of from about 0.1 to about 2.5 weight percent, based on a total weight of the agent.

18. The method of claim 12, wherein:
the (A) at least one oxidation dye precursor, (B) the glucoheptonic acid, and (C) the at least one oxidizing agent are components of the agent, and wherein
applying the components of the agent further comprises applying the components of the agent one after the other to the keratinous fibers, without rinsing between the application of the components of the agent.

19. The agent according to claim 1, wherein the agent comprises—based on its total weight—the glucoheptonic acid or at least one of its physiologically tolerated salts and/or lactones in a total amount of from about 0.1 to about 0.5% by weight, the amount being based on the weight of free glucoheptonic acid in relation to the weight of the agent.

20. The agent according to claim 1, wherein the at least one oxidation dye precursor of structure (I) comprises 4,5-diamino-1-(2-hydroxyethyl)-1H-pyrazole sulfate.

* * * * *